US007819911B2

(12) United States Patent
Anderson et al.

(10) Patent No.: US 7,819,911 B2
(45) Date of Patent: Oct. 26, 2010

(54) MULTIFUNCTION WARMING DEVICE FOR PERIOPERATIVE USE

(75) Inventors: Thomas P. Anderson, Savage, MN (US); Shad N. Lindrud, Albertville, MN (US); Gary R. Maharaj, Eden Prairie, MN (US); Carol J. Panser, St. Louis Park, MN (US); Mark J. Scott, Maple Grove, MN (US); Teryl L. Woodwick Sides, Maple Grove, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1042 days.

(21) Appl. No.: 11/583,432

(22) Filed: Oct. 19, 2006

(65) Prior Publication Data

US 2007/0093882 A1    Apr. 26, 2007

Related U.S. Application Data

(60) Provisional application No. 60/729,000, filed on Oct. 20, 2005, provisional application No. 60/835,602, filed on Aug. 4, 2006.

(51) Int. Cl.
*A61F 7/00* (2006.01)
(52) U.S. Cl. .................................. 607/107; 607/104
(58) Field of Classification Search .................. 607/104, 607/107–114; 2/114, 456, 458
See application file for complete search history.

(56) References Cited

U.S. PATENT DOCUMENTS

| 2,512,559 A | 6/1950 | Williams | 5/347 |
| 2,573,414 A | 10/1951 | Dunn | 128/144 |
| 2,826,758 A | 3/1958 | Kahn | 2/81 |
| 3,468,299 A | 9/1969 | D'Amato | 126/204 |
| 3,610,323 A | 10/1971 | Troyer | 165/46 |
| 3,757,366 A | 9/1973 | Sacher | 5/347 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |

(Continued)

FOREIGN PATENT DOCUMENTS

FR   821150   11/1937

(Continued)

OTHER PUBLICATIONS

EPO Examination Report mailed Dec. 17, 2007, in EP03719690.4-1526, EP Regional Phase of PCT/US2003/11128 (published as WO/2003/086500).

(Continued)

*Primary Examiner*—Roy D Gibson
(74) *Attorney, Agent, or Firm*—Terrance A. Meador; INCAPLAW

(57) ABSTRACT

A multifunction warming device for perioperative use includes a clinical garment and two convective warming apparatuses supported on an inside surface of the clinical garment. A first convective apparatus is disposed transversely in an upper portion of the clinical garment, running between sleeves of the clinical garment. The second convective apparatus is disposed longitudinally in a lower portion of the clinical garment and has separately inflatable sections, each for enabling a particular mode of warming.

25 Claims, 11 Drawing Sheets

U.S. PATENT DOCUMENTS

| | | | |
|---|---|---|---|
| 4,369,528 A | 1/1983 | Vest et al. ............... | 2/69 |
| 4,494,248 A | 1/1985 | Holder ............... | 2/69 |
| 4,524,463 A | 6/1985 | Ogden ............... | 2/105 |
| 4,558,468 A | 12/1985 | Landry et al. ............... | 2/51 |
| 4,578,825 A | 4/1986 | Vote ............... | 2/114 |
| 4,587,671 A | 5/1986 | Rodriguez, Jr. et al. ...... | 2/69 |
| 4,651,727 A | 3/1987 | Howorth ............... | 128/201.23 |
| 4,653,120 A | 3/1987 | Leaf ............... | 2/114 |
| 4,696,066 A | 9/1987 | Ball et al. ............... | 2/272 |
| 4,718,124 A | 1/1988 | Sawicki et al. ............... | 2/114 |
| 4,787,101 A | 11/1988 | Feinberg ............... | 2/105 |
| 4,914,752 A | 4/1990 | Hinson et al. ............... | 2/2 |
| 4,964,282 A | 10/1990 | Wagner ............... | 62/259.3 |
| 5,062,424 A | 11/1991 | Hooker ............... | 128/379 |
| 5,190,031 A | 3/1993 | Guibert et al. ............... | 62/259.3 |
| 5,255,390 A | 10/1993 | Gross et al. ............... | 2/2 |
| 5,304,213 A | 4/1994 | Berke et al. ............... | 607/107 |
| 5,360,439 A | 11/1994 | Dickerhoff et al. ............... | 607/107 |
| 5,367,710 A | 11/1994 | Karmin ............... | 2/114 |
| 5,411,541 A | 5/1995 | Bell et al. ............... | 607/104 |
| 5,443,488 A | 8/1995 | Namenye et al. ............... | 607/107 |
| 5,572,742 A | 11/1996 | McFadden ............... | 2/114 |
| 5,575,006 A | 11/1996 | Wolfe ............... | 2/114 |
| 5,611,087 A | 3/1997 | Adkins ............... | 2/114 |
| 5,620,482 A | 4/1997 | Augustine et al. ............... | 607/107 |
| 5,697,963 A | 12/1997 | Augustine ............... | 607/108 |
| 5,733,318 A | 3/1998 | Augustine ............... | 607/104 |
| 5,749,109 A | 5/1998 | Kappel ............... | 5/423 |
| 5,785,716 A | 7/1998 | Bayron ............... | 607/108 |
| 5,891,187 A | 4/1999 | Winthrop et al. ............... | 607/96 |
| 5,946,722 A | 9/1999 | Trautmann ............... | 2/83 |
| 5,970,519 A | 10/1999 | Weber ............... | 2/81 |
| 5,974,605 A | 11/1999 | Dickerhoff et al. ............... | 5/421 |
| 6,049,907 A | 4/2000 | Palomo ............... | 2/51 |
| 6,154,883 A | 12/2000 | Spann et al. ............... | 2/69 |
| 6,156,058 A | 12/2000 | Kappel et al. ............... | 607/107 |
| 6,203,567 B1 | 3/2001 | Augustine ............... | 607/104 |
| 6,216,270 B1 | 4/2001 | Moquin et al. ............... | 2/69 |
| 6,235,659 B1 | 5/2001 | McAmish et al. ............... | 442/79 |
| 6,378,136 B2 | 4/2002 | Matsushita ............... | 2/114 |
| 6,484,321 B1 | 11/2002 | Shamam ............... | 2/114 |
| 6,511,501 B1 | 1/2003 | Augustine et al. ............... | 607/96 |
| 6,524,332 B1 | 2/2003 | Augustine et al. ............... | 607/107 |
| 6,551,347 B1 | 4/2003 | Elkins ............... | 607/104 |
| 6,571,574 B1 | 6/2003 | Blackstone ............... | 62/420 |
| 6,596,019 B2 | 7/2003 | Turner et al. ............... | 607/108 |
| 6,647,552 B1 | 11/2003 | Hogan ............... | 2/114 |
| 6,694,522 B1 | 2/2004 | Neal ............... | 2/114 |
| 6,792,622 B2 | 9/2004 | Graves ............... | 2/114 |
| 6,799,332 B2 | 10/2004 | Hatton ............... | 2/114 |
| 6,820,622 B1 | 11/2004 | Teves et al. ............... | 128/849 |
| 6,851,125 B2 | 2/2005 | Fujikawa et al. ............... | 2/51 |
| 6,876,884 B2 | 4/2005 | Hansen et al. ............... | 607/98 |
| 7,001,416 B2 | 2/2006 | Augustine et al. ............... | 607/104 |
| 7,089,995 B2 * | 8/2006 | Koscheyev et al. ............... | 165/46 |
| 7,226,454 B2 | 6/2007 | Albrecht et al. ............... | 607/104 |
| 7,276,076 B2 | 10/2007 | Bieberich ............... | 607/108 |
| 7,364,584 B2 | 4/2008 | Anderson ............... | 607/108 |
| 7,373,969 B2 * | 5/2008 | Chambers ............... | 165/297 |
| 7,470,280 B2 | 12/2008 | Bieberich ............... | 607/104 |
| 2003/0126668 A1 | 7/2003 | Scroggins ............... | 2/114 |
| 2005/0015127 A1 | 1/2005 | Bieberich ............... | 607/104 |
| 2005/0143796 A1 | 6/2005 | Augustine et al. ............... | 607/104 |
| 2006/0047332 A1 | 3/2006 | Malmberg et al. ............... | 607/104 |
| 2006/0122671 A1 | 6/2006 | Albrecht et al. ............... | 607/104 |
| 2006/0122672 A1 | 6/2006 | Anderson ............... | 607/104 |
| 2006/0147320 A1 | 7/2006 | Hansen et al. ............... | 417/313 |
| 2006/0184216 A1 | 8/2006 | Van Duren ............... | 607/104 |
| 2006/0184217 A1 | 8/2006 | Van Duren ............... | 607/104 |
| 2006/0184218 A1 | 8/2006 | Bieberich ............... | 607/104 |
| 2006/0259104 A1 | 11/2006 | Panser ............... | 607/104 |
| 2007/0093883 A1 | 4/2007 | Anderson et al. ............... | 607/104 |
| 2007/0093884 A1 | 4/2007 | Anderson et al. ............... | 607/104 |
| 2007/0093885 A1 | 4/2007 | Anderson et al. ............... | 607/104 |
| 2007/0239239 A1 | 10/2007 | Albrecht et al. ............... | 607/96 |
| 2008/0027521 A1 | 1/2008 | Bieberich ............... | 607/96 |
| 2008/0027522 A1 | 1/2008 | Bieberich ............... | 607/96 |
| 2008/0125840 A1 | 5/2008 | Anderson ............... | 607/96 |
| 2008/0177361 A1 | 7/2008 | Anderson ............... | 607/108 |
| 2009/0062891 A1 | 3/2009 | Bieberich ............... | 607/104 |
| 2009/0149931 A9 | 6/2009 | Anderson ............... | 607/104 |
| 2009/0228083 A1 | 9/2009 | Anderson et al. ............... | 607/107 |

FOREIGN PATENT DOCUMENTS

| | | |
|---|---|---|
| GB | 475811 | 11/1937 |
| GB | 1 462 033 | 1/1997 |
| SE | 525415 | 2/2005 |
| WO | WO 97/14381 A1 | 4/1997 |
| WO | WO 98/48652 | 11/1998 |
| WO | WO 00/62726 | 10/2000 |
| WO | WO 03/086500 A3 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

EPO Examination Report mailed Sep. 2, 2008, in EP05789978.3, EP Regional Phase of PCT/US2005/025355 (published as WO/2006/020170).

EPO Examination Report mailed Jan. 23, 2009, in EP05853202, EP Regional Phase of PCT/US2005/044214 (published as WO/2006/063027).

International Search Report and Written Opinion in PCT/US2008/000141, mailed Nov. 11, 2008.

International Search Report and Written Opinion in PCT/US2005/025355, mailed Dec. 1, 2005.

International Search Report and Written Opinion in PCT/US2005/043968, mailed Apr. 19, 2006.

International Search Report and Written Opinion in PCT/US2005/044214, mailed Apr. 19, 2006.

P.O. Fanger, Thermal Comfort: Analysis and Applications in Environmental Engineering, Danish Technical Press, 1970, pp. 5-67.

C.B. Mahony & J. Odom, Maintaining intraoperative normothermia: A meta-analysis of outcomes with costs. *AANA Journal*. Apr. 1999. vol. 67, No. 2:155-164.

Porta-Chill—The Portable Air-Chiller—Brochure, http://www.portachil.com/, Dec. 3, 2002.

EPO Examination Report mailed Oct. 24, 2006, in EP03719690.4-1526, EP Regional Phase of PCT/US2003/11128 (published as WO/2003/086500).

International Search Report and Written Opinion in PCT/US2007/013073, mailed Nov. 9, 2007.

International Search Report & Written Opinion in PCT/US2006/041028, mailed Feb. 20, 2007.

EPO Examination Report mailed Jan. 8, 2008, in EP05853005.6, EP Regional Phase of PCT/US2005/043968 (published as WO/2006/062910).

EPO Examination Report mailed Apr. 24, 2009, in EP06826351.6, EP Regional Phase of PCT/US2006/041028 (published as WO/2007/047917).

EPO Examination Report mailed Jun. 22, 2009, in EP05853202.9, EP Regional Phase of PCT/US2005/043968 (published as WO/2006/062910).

Applicants' response to the Examination Report in EP06826351.6, mailed Aug. 20, 2009.

EPO Examination Report mailed Sep. 3, 2009 in EP 07795671.2, EP Regional Phase of PCT/US2007/013073 (published as WO/2008/013603).

EPO Examination Report mailed Sep. 29, 2009, in EP06720577.3, EP Regional Phase of PCT/US2006/004644 (published as WO/2006/086587).

EPO Examination Report mailed Apr. 14, 2010 in EP06826351.6, EP Regional Phase of PCT/US2006/041028 (published as WO/2007/047917).

Written Opinion of the International Search Authority (EPO) in PCT/US2006/041028, mailed Feb. 20, 2007.

International Search Report and Written Opinion in PCT/US2006/004644, mailed Dec. 18, 2006.

* cited by examiner

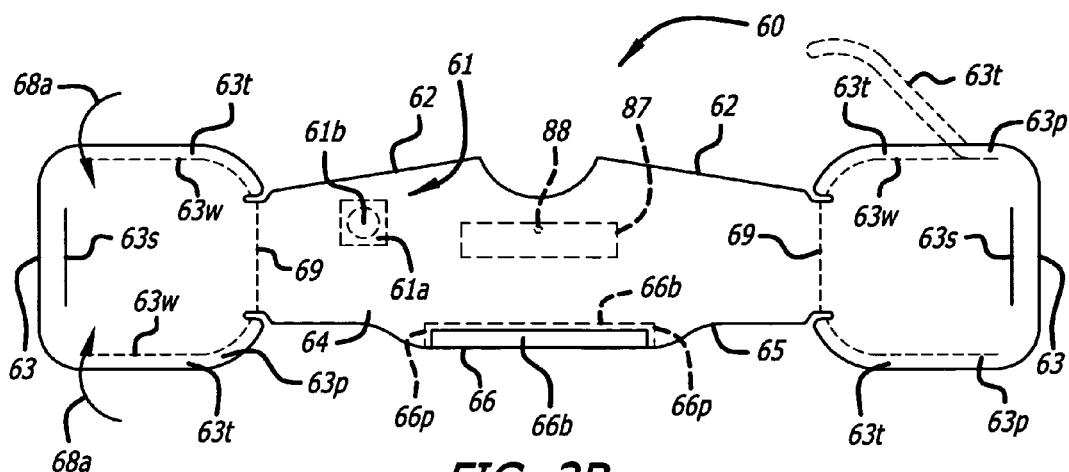
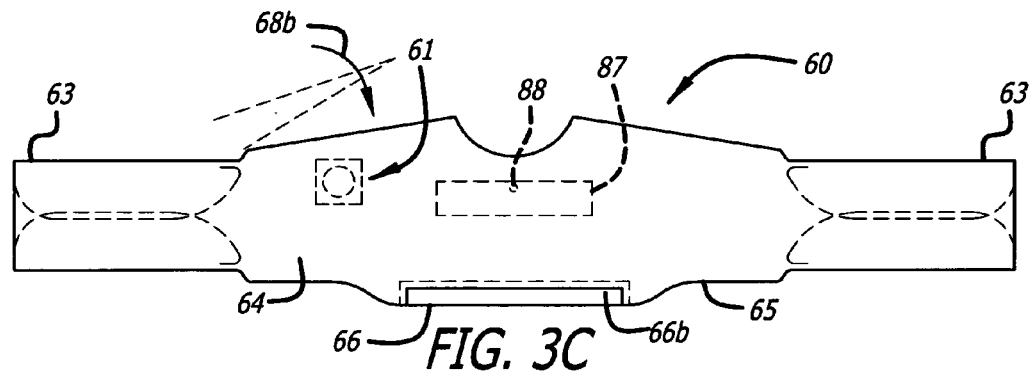
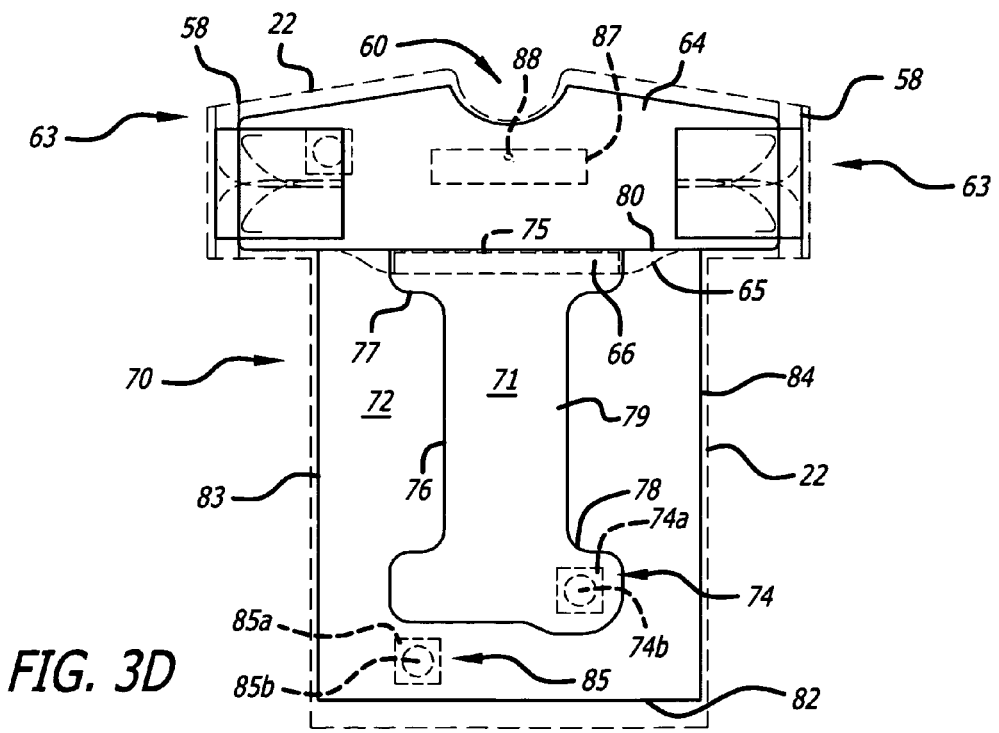

MULTIFUNCTION WARMING DEVICE FOR PERIOPERATIVE USE

RELATED APPLICATIONS

This application claims priority to U.S. Provisional patent application 60/729,000, filed Oct. 20, 2005 and to U.S. Provisional patent application 60/835,602, filed Aug. 4, 2006.

This application contains subject matter related to the subject matter of the following patent applications, all commonly owned herewith and all incorporated by reference:

Patent Cooperation Treaty (PCT) Application No. PCT/US03/011128, filed Apr. 10, 2003, entitled "Patient Comfort Apparatus and System", and published on Oct. 23, 2003 under Publication No. WO 2003/086500;

Patent Cooperation Treaty (PCT) Application No. PCT/US05/025355, filed Jul. 18, 2005, entitled "Perioperative Warming Device", and published on Feb. 23, 2006 under Publication No. WO 2006/020170;

Patent Cooperation Treaty (PCT) Application No. PCT/US05/043968, filed Dec. 6, 2005, entitled "Warming Device with Varied Permeability", and published on Jun. 15, 2006 under Publication No. WO 2006/062910;

Patent Cooperation Treaty (PCT) Application No. PCT/US05/044214, filed Dec. 6, 2005, entitled "Warming Device", and published on Jun. 15, 2006 under Publication No. WO 2006/063027;

Patent Cooperation Treaty (PCT) Application No. PCT/US06/004644, filed Feb. 9, 2006, entitled "Warming Device for Perioperative Use", and published on Aug. 17, 2006 under Publication No. WO 2006/086587;

U.S. patent application Ser. No. 10/411,865, filed Apr. 10, 2003, entitled "Patient Comfort Apparatus and System" and published on Oct. 16, 2003 under Publication No. US 2003/0195596 and issued on Feb. 21, 2006 under U.S. Pat. No. 7,001,416;

U.S. patent application Ser. No. 10/508,319, filed Sep. 20, 2004, entitled "Patient Comfort Apparatus and System" and published on Jun. 30, 2005 under Publication No. US 2005/0143796;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672;

U.S. patent application Ser. No. 11/057,396, filed Feb. 11, 2005, entitled "Perioperative Warming Device", and published on Aug. 17, 2006 under Publication No. US 2006/0184215, now U.S. Pat. No. 7,276,076;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218; and, U.S. patent application Ser. No. 11/363,136, filed Feb. 27, 2006, entitled "Forced Air Warming Unit" and published on Jul. 6, 2006 under Publication No. US2006/0147320;

This application also contains subject matter related to the subject matter of the following patent applications, all commonly owned and filed concurrently herewith:

PCT Application No. US/2006/041028, filed Oct. 19, 2006, entitled "Multifunction Warming Device for Perioperative Use", and published on Apr. 26, 2007 under Publication No. WO2007/047917;

PCT Application No. PCT/US2007/013073, filed Jun. 1, 2007, entitled "Warming Device";

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/057,397, filed Feb. 11, 2005, entitled "Thermal Blanket for Warming the Limbs", and published on Aug. 17, 2006 under Publication No. US 2006/0184216;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,477, filed Oct. 19, 2006, entitled "Multifunction Warming Device with Provision for Being Secured", and published on Apr. 26, 2007 under Publication No. US 2007/0093883;

U.S. patent application Ser. No. 11/583,480, filed Oct. 19, 2006, entitled "Multifunction Warming Device with Provision for Warming Hands", and published on Apr. 26, 2007 under Publication No. US 2007/0093884;

U.S. patent application Ser. No. 11/583,481, filed Oct. 19, 2006, entitled "Multifunction Warming Device with an Upper Body Convective Apparatus", and published on Apr. 26, 2007 under Publication No. US 2007/0093885;

U.S. patent application Ser. No. 11/656,777, filed Jan. 23, 2007, entitled "Convective Warming Device With a Drape";

U.S. patent application Ser. No. 11/704,547, filed Feb. 9, 2007, entitled "A Forced Air Warming Unit";

U.S. patent application Ser. No. 11/801,292, filed May 9, 2007, entitled "Warming Device with Varied Permeability", and published on Oct. 11, 2007 under Publication No. US 2007/023939;

U.S. patent application Ser. No. 11/899,872, filed Sep. 7, 2007, entitled "Perioperative Warming Method"; and U.S. patent application Ser. No. 11/899,928, filed Sep. 7, 2007, entitled "Perioperative Warming Device".

BACKGROUND

A multifunction warming device for perioperative use includes a clinical garment with two or more convective warming apparatuses supported on the inside of the garment. At least one convective apparatus has separately inflatable sections, each for enabling a particular mode of warming.

In this specification, use of the term "convective" to denote the transfer of heat from a device to a body refers to the device's principal mode of heat transfer, it being understood that heat may at the same time be transferred from the device to the body by conduction and radiation, although not to the degree of convection.

Convective devices that transfer heat to a human body are known. For example, there are devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These devices are typically called "convective thermal blankets" or "covers"; for convenience, in this discussion and the following specification, they shall be called, simply, "thermal blankets." Arizant Healthcare Inc., the assignee of this application, makes and sells such devices under the BAIR HUGGER® brand. One such device is the Model 522 Upper Body Blanket.

Thermal blankets have been specifically designed for particular deployments where therapeutic warming is indicated. Three representative thermal blankets known in the prior art are shown in FIGS. 1A-1D. A "full body" thermal blanket 10 is shown in FIG. 1A. The full body thermal blanket is adapted to lie upon a person and to extend longitudinally along the body of the person in order to cover substantially the person's entire body, from near the ankles or feet up to the neck. A "lower body" thermal blanket 12 is shown in FIG. 1B. The lower body thermal blanket 12 is adapted to lie upon the person and to extend longitudinally along the body of a person in order to cover the person's lower body, from near the ankles or feet up to the waist or pelvis of the person. An "upper body" thermal blanket 15 is illustrated in FIGS. 1C and 1D. The upper body thermal blanket 15 has a bow-tie shape that is adapted to lie upon and extend transversely across the upper body of a person in order to cover the person's chest and extended arms. A head drape 16 may be formed on or attached to the upper body thermal blanket 15 for draping over the head 17 of a person in order to retain warmed air expelled through the blanket 15 about the head to aid in therapeutic warming during surgery. When fed a stream of warmed pressurized air, each of the thermal blankets 10, 12, 15 inflates and distributes the air within itself. While the thermal blanket lies on the person, the warmed pressurized air flows through apertures or interstices in a permeable surface of the thermal blanket which faces the person. These thermal blankets may have one, two, or more inlet ports 18 through which an air hose 19 provides warmed pressurized air from a heater/blower unit (not shown in these drawings).

The construction of prior art thermal blankets is well understood. Examples of specific constructions are given in U.S. Pat. No. 5,620,482, U.S. Pat. No. 5,443,488, U.S. Pat. No. 5,360,439, and U.S. Pat. No. 5,304,213. See also U.S. Pat. No. 5,974,605.

An invention covering a warming device is disclosed in the referenced Publication No. WO 2003/086500 wherein a clinical garment such as a robe or gown is adapted to support a convective apparatus in order to warm a person wearing the garment for comfort and mobility of the person. An invention covering a multifunction warming device for perioperative use is described in the referenced Publication US 2006/0122671 wherein a warming device is constituted of a clinical garment and a convective apparatus adapted for comfort and therapeutic warming that is supported on the inside surface of the garment.

The term "perioperative" is defined in the PDR Medical Dictionary, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. AANA Journal. 4/99; 67, 2:155-164.), therapeutic warming is employed during at least the intraoperative period in order to prevent or mitigate effects that result from hypothermia. In fact, it is increasingly manifest that maintenance of normothermia perioperatively enhances the prospects for a quick, successful recovery from surgery. For example, maintenance of perioperative normothermia appears to be a factor in decreasing the incidence of surgical wound infections in patients undergoing colorectal surgery, (Kurz A, Sessler D I, Lenhardt R. Perioperative normothermia to reduce the incidence of surgical-wound infection and shorten hospitalization. Study of Wound Infection and Temperature Group. N Engl J Med. May 9, 1996; 334(19):1209-1215). Other studies suggest that maintenance of perioperative normothermia improves surgical outcomes at low cost, (Harper C M, McNicholas T, Gowrie-Mohan S. Maintaining perioperative normothermia. BMJ. Apr. 5, 2003; 326(7392):721-722). The effectiveness of therapeutic warming depends upon delivery of enough heat to a patient's body to raise the patient's core body temperature to, or maintain it within, a narrow range, typically around 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect; and, comfort warming may have some therapeutic effect. However, even though thermal comfort is a subjective notion, environmental conditions that produce a sense of thermal comfort in a population of human beings are known and well tabulated. For example, Fanger (Thermal Comfort: Analysis and Applications of Environmental Engineering, Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Therapeutic warming is typically provided by convective devices such as the thermal blankets shown in FIGS. 1A-1D. An example of use of a full body thermal blanket for therapeutic warming is found in U.S. Pat. No. 6,524,332, "System and Method for Warming a Person to Prevent or Treat Hypothermia", commonly owned with this application. Comfort warming by convective means is described in the referenced Publication No. WO 2003/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced-air warming unit, a heater unit, etc.), a convective device (which is, typically, inflatable), and a flexible conduit or air hose connecting the heater/blower unit with the convective device. Use of such a system for a particular type of warming requires delivery of warmed air through a convective device at parametric values that achieve a particular objective. For example, for comfort warming, the temperature at the hose end, prior to the air entering the convective device, may range from ambient to 42° C. (WO 2003/086500 at page 11, lines 24-26). The conditions by which a convective device such as a thermal blanket produces thermal comfort in normothermic individuals at steady state are significantly different from those necessary to treat hypothermia. Typically the conditions for thermal comfort are met in a system with a relatively low capacity heater/blower unit that delivers a stream of air at one combination of pressure and temperature, while those in a therapeutic warming system are achieved with a relatively high capacity heater/blower unit that delivers a stream of air at another combination of pressure and temperature. Alternatively, a single heater/blower unit may be provided with controls that enable it to adjust the combination of air pressure and temperature in order to vary its operation between support of comfort and therapeutic warming.

Health care cost is an issue of national importance. The cost of warming perioperatively is directly related to the number of perioperative periods in which a person is warmed; the cost increases when different warming apparatus are used in different periods to accomplish different goals. Mobility, comfort, and therapy have recently been combined in warming configurations described in the related applications that are identified above. However, there is currently no single warming device configuration that affords all of the options for therapeutic warming that are available in the set of thermal blankets illustrated in FIGS. 1A-1D.

For example, the upper body thermal blanket 15 shown in FIGS. 1C and 1D is frequently used during thoracic, abdominal and pelvic surgery. As is known, a patient's core body temperature can drop to hypothermic levels quickly during such surgery. To prevent or mitigate the effects of hypothermia, an upper body blanket might be deployed for therapeutic warming during the surgery, especially if it is lengthy. If warmed preoperatively with a comfort warming device described in WO 2003/086500, or with a perioperative warming device described in US 2006/0122671, the patient will have the warming device on up to the time when surgery commences. But, in both cases, the clinical garment is removed from the patient prior to surgery in order to provide access to the surgical site and to the patient's upper body for therapeutic warming. Concurrently, an upper body thermal blanket must be unpackaged, made ready and deployed warming during for surgery. Following surgery, warming may be indicated for therapy (mitigation of hypothermia, for example) or comfort, in which case either the warming device used preoperatively, another warming device, or a thermal blanket must be deployed on the patient. Manifestly, substantial convenience and a significant reduction in cost would result from perioperative use of a single multifunction warming device capable of clothing a patient and providing comfort warming preoperatively, manifold therapeutic warming intraoperatively (including during thoracic, abdominal and pelvic surgery), and optional therapeutic or comfort warming postoperatively.

SUMMARY

A multifunction warming device includes a clinical garment having an inside surface supporting two convective devices. One convective device is disposed to be inflated so as to provide therapeutic warming during thoracic, abdominal, and pelvic surgery, without removal of the warming device from the person wearing the warming device. The other convective device has multiple, separately inflatable sections. At least one section may be operated to provide comfort warming to a person wearing the clinical garment, and at least another section may be operated to provide therapeutic warming during surgery on the upper body.

BRIEF DESCRIPTION OF THE DRAWINGS

FIGS. 3B and 3C are plan views of a first convective apparatus to provide therapeutic warming in a multifunction warming device. FIG. 3C shows details of folding elements of the first convective apparatus.

FIG. 3D is a plan view of the first convective apparatus of FIGS. 3B and 3C overlapped by a second convective apparatus having separately inflatable sections.

SPECIFICATION

A multifunction warming device for perioperative use is constituted of a clinical garment and two or more convective warming apparatuses (hereinafter, "convective apparatuses") supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. A convective apparatus receives and distributes at least one stream of warmed pressurized air in a structure for being disposed on, adjacent, or next to the core and/or the limbs of a body. When pressurized with warmed air, a convective apparatus emits warmed air through one or more of its surfaces.

In one aspect, a multifunction warming device for perioperative use may be worn on a person where it receives a stream of warmed pressurized air, distributes the pressurized air within one of the convective apparatuses, and emits the air through one or more surfaces of the convective apparatus to warm the person's body.

In another aspect, the multifunction warming device may be adapted for therapeutic warming during surgery. In this regard, the multifunction warming device may be adapted for therapeutic warming by deploying one of the convective apparatuses for use intraoperatively while the clinical garment and the unused convective apparatus are furled and positioned so as not to intrude on the surgical site.

In the warming device illustrated and discussed below, the convective apparatuses are inflatable. That is, their structures, flaccid when not in use, tauten when receiving a stream of pressurized air.

Figure 1A:
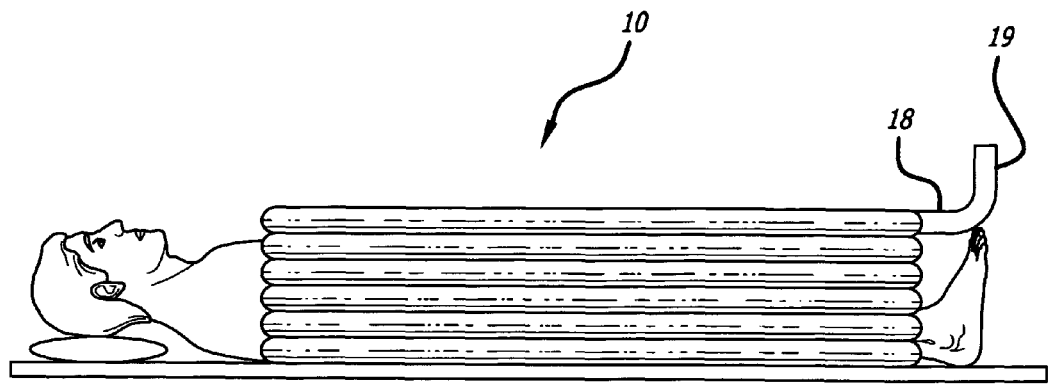
FIGS. 1A-1D are illustrations of prior art full body, lower body, and upper body convective thermal blankets.
Figure 1B:
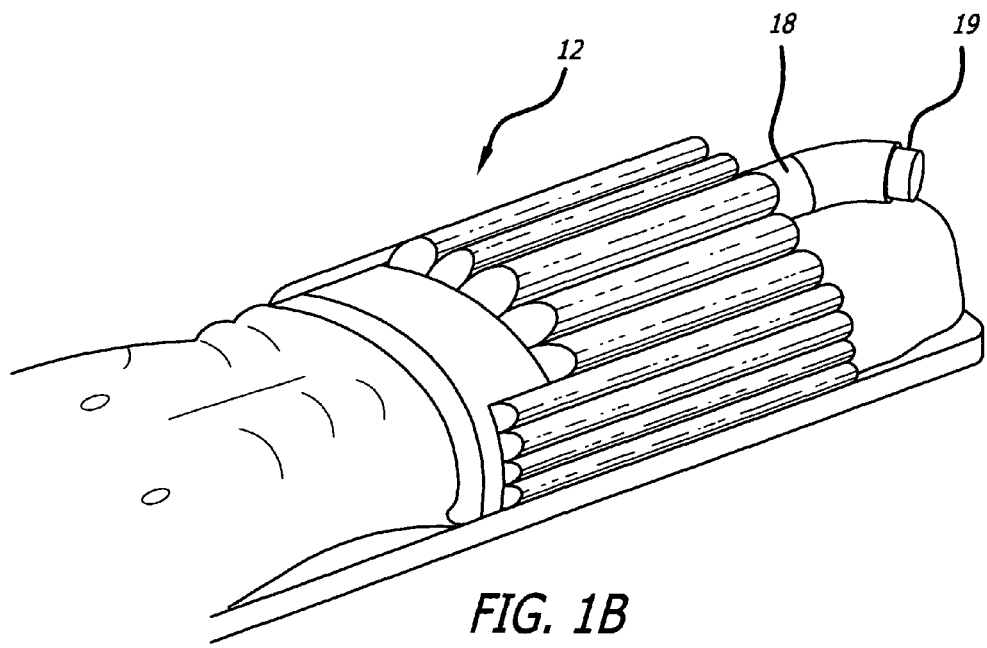
Figure 1C:
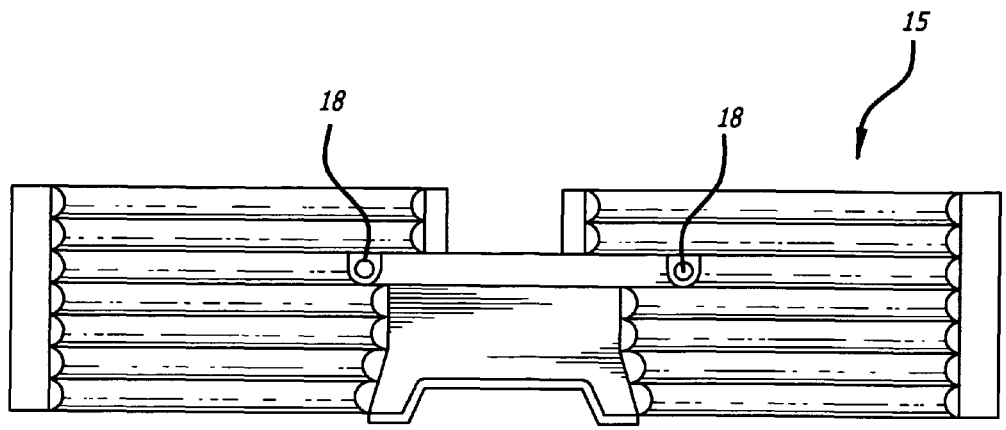
Figure 1D:
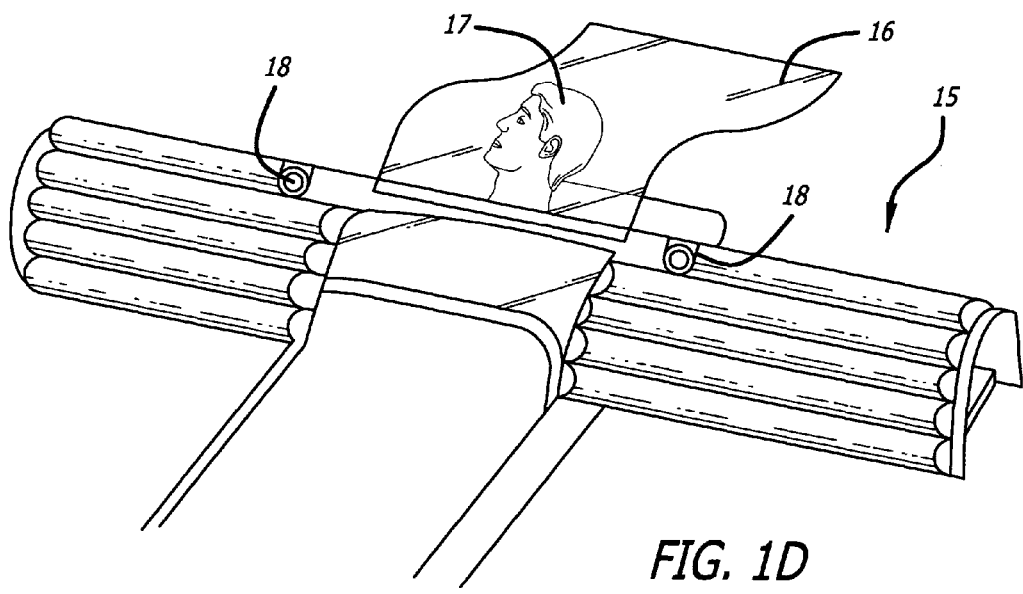
Figure 2:
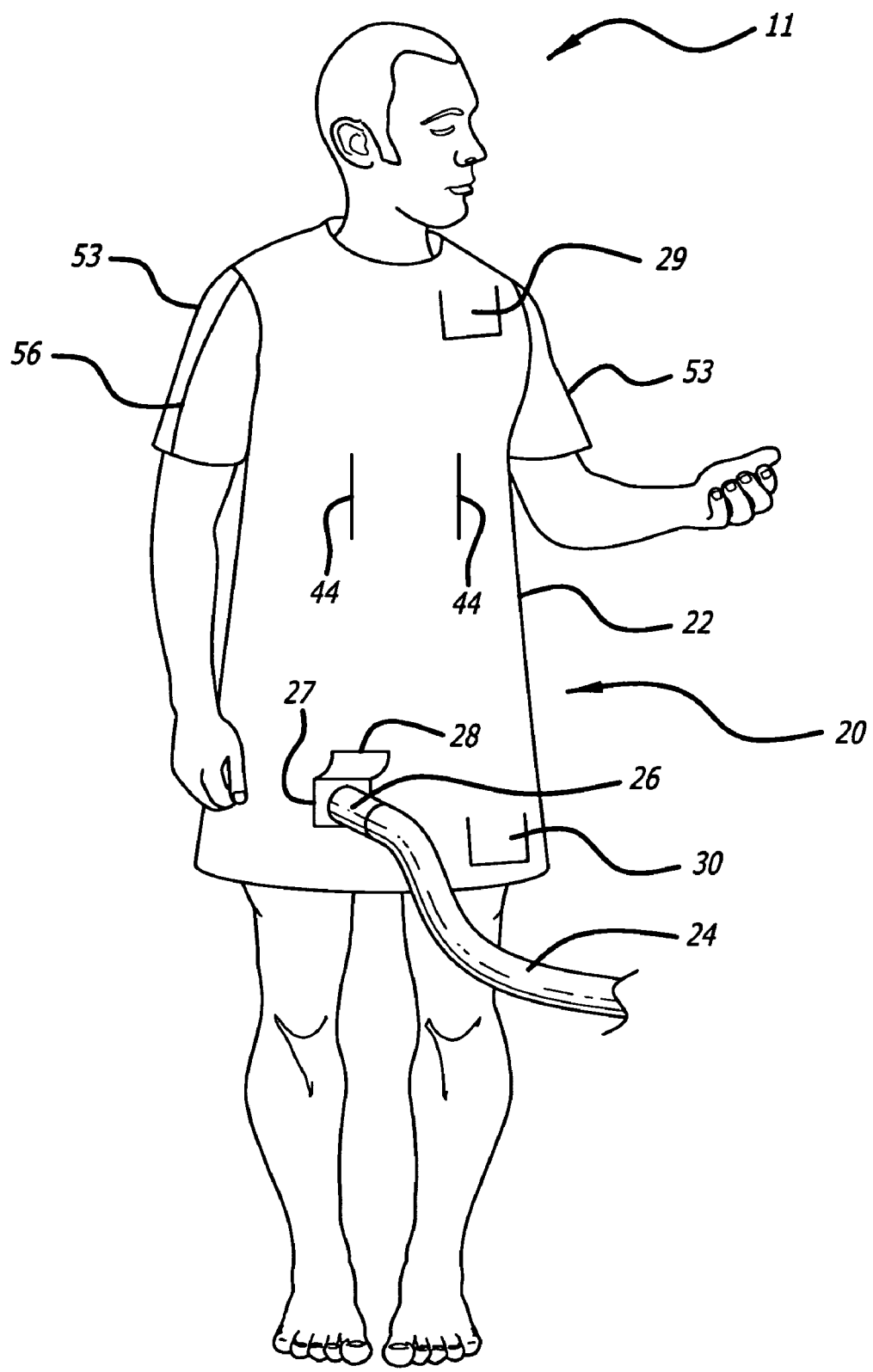
FIG. 2 is an illustration of a person wearing a multifunction warming device for perioperative use.

Refer now to the figures, in which a person 11 wearing a multifunction warming device 20 for perioperative use is illustrated in FIG. 2. The warming device 20 is constituted of a clinical garment 22 and two or more convective apparatuses (not seen in this view) that are supported on an inside surface of the clinical garment 22. Either convective apparatus may be operated by receiving warmed, pressurized air from a heater/blower unit (not seen in this view) through an air hose with a nozzle that is received in an inlet port of the convective apparatus. One such air hose 24, with a nozzle 26, is shown in FIG. 2. One such inlet port is indicated by reference numeral 27 in FIG. 2. The inlet port 27 is accessed through a flap 28 in the clinical garment 22. Other convective apparatus inlet ports may be accessed through other flaps in the clinical garment 22 such as flaps 29 and 30.

Figure 3A:
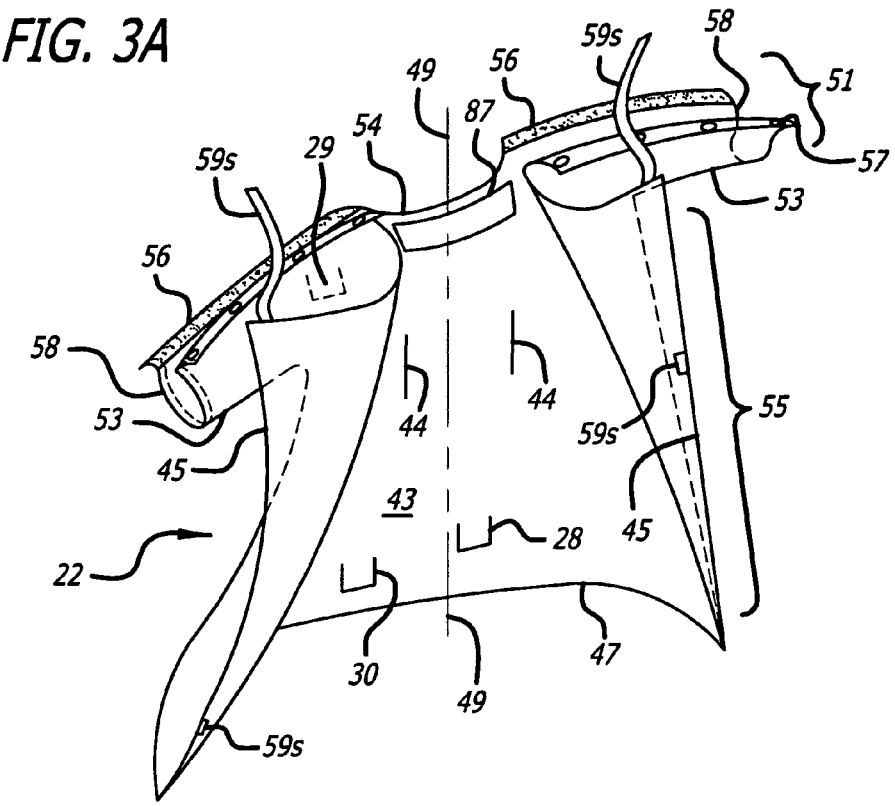
FIG. 3A is a perspective view from behind a clinical garment, with the clinical garment partially opened to show an inside surface that supports two convective warming apparatuses.
Figure 3F:
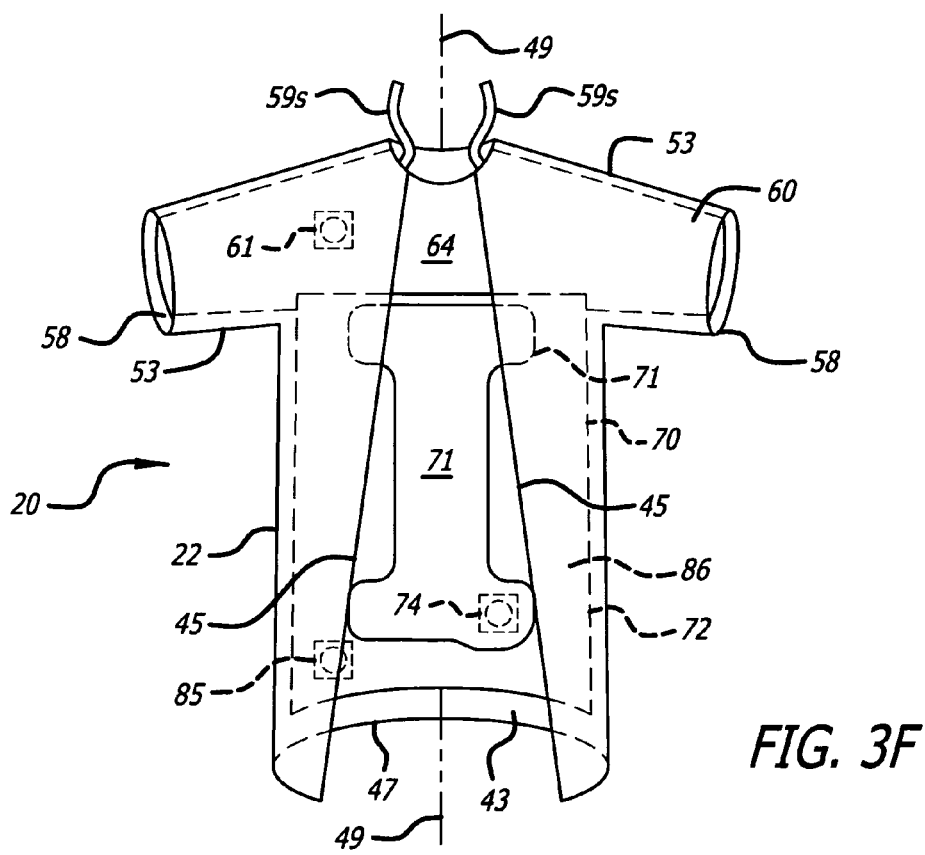
FIG. 3F is a rear elevation view of a multifunction warming device for perioperative use.

FIGS. 3A-3D illustrate the elements of a multifunction warming device for perioperative use; the assembled multifunction warming device 20 is itself illustrated in FIG. 3F. The view in FIGS. 3A and 3F is from the rear of the clinical garment 22, looking toward the inside surface of the garment, which faces the chest, or thorax of a patient and on which the two convective apparatuses are mounted. FIGS. 3B through 3D are plan views of uninflated convective apparatuses, looking toward the permeable surfaces through which air is expelled toward a patient when the blankets are inflated. As seen in FIGS. 3A and 3F, the warming device 20 includes the clinical garment 22. The clinical garment 22 includes an inside surface 43, two slits 44 (also seen in FIG. 2), two opposing lateral hems 45, a lower hem 47, and a longitudinal axis 49. The clinical garment 22 has an upper portion 51 with two opposing sleeves 53 (also seen in FIG. 2) and a scooped upper edge 54, and a lower portion 55. The flaps 28, 29, and 30 that provide access to inlet ports through the front of the garment 22 are also visible in FIG. 3A. The sleeves 53 may be long or short. Short sleeves are preferred if access must be had to a person's arms for instrumentation and/or IV delivery. Each sleeve 53 includes an elongate seam 56 (both seen closed in FIG. 2). Each seam 56 may be held closed by means 57 including, for example, buttons, snaps, hook and loop material, tape, and/or straps, or any equivalent thereof. Such means can be operated to let seam 56 be opened and to again close a seam, once opened. Cuffs 58 may be formed in the clinical garment 22 inside the sleeves 53, near the ends of the sleeves 53. The clinical garment 22 may open on a side. Preferably, the clinical garment 22 opens in the rear. The opening may be full, as illustrated in FIG. 3A, or it may be a slit rising from the lower hem 47. As per the example shown in FIG. 3A, the opening may be closed by means 59 along the lateral hems 45 which releasably connect to keep the hems together. Such means may include, for example, buttons, snaps, hook and loop material, tape, and/or straps, or any equivalent thereof. In keeping with the example of FIG. 3A, if straps are used to close the opening, the straps may be attached to the clinical garment 22, or formed integrally therewith as a step in manufacturing the clinical garment 22. For example only, two integrally-formed straps 59s for tying the opposing lateral hems 45 together in the upper portion 51 are seen in FIG. 3A. Two additional straps may be attached to the outside surface of the clinical garment 22 with enough reach to be tied together around the outside of the clinical garment, near its middle. With enough overlap of the lateral hems 45, the opening in the clinical garment 22 can be completely closed and secured, with the lateral hems overlapping to afford concealment of a patient's private parts. The clinical garment 22 may be constructed from nonwoven or woven materials. Preferably, the clinical garment 22 is made from a non-woven blend of spunlace polyester and wood pulp.

In FIG. 3B, a first convective apparatus 60 is shown fully opened for deployment to provide therapeutic warming. In FIG. 3C, elements of the first convective apparatus 60 are shown folded. The view in both figures is toward a permeable surface of the convective apparatus 60 through which heated air is expelled when the blanket is inflated. As seen in these figures, the first convective apparatus 60 includes an inlet port 61, two laterally-extending arms 62, each transitioning to a respective end 63, a permeable surface 64, and a lower edge 65. Each end 63 has a generally quadrilateral configuration with a periphery 63p. Typically, the periphery 63p includes a seal with some width. In some aspects of the first convective apparatus 60, ties 63t may be integrally formed or defined in the peripheries 63p by lines of weakness or perforations 63w. One tie 63t is shown in dashed outline in FIG. 3B partially separated from the periphery 63p in which it is formed. Such ties may be used when the first convective apparatus 60 is deployed for use in securing the first convective apparatus 60. As can be appreciated, from the separated tie 63t, the arcuate shape near the end of the tie provides easy handling for tying to another tie, to a patient, or to equipment in the surgical area. See the assignee's U.S. Pat. No. 5,773,275 in this regard. Optionally, slits 67s may be formed in seals near the outer edges of the ends 63. The slits 63s may be defined in the seals by lines of perforations. If provided, the slits 63s may be opened to be used as purchase holds for unfurling the ends 63 and/or for receiving the hands on the outstretched arms of a patient in order to anchor or secure the ends 63 such as when the first convective apparatus 60 is inflated and operated.

For stowing the first convective apparatus 60 prior to use, the opposing sides of the ends 63 may be folded toward each other as indicated by the arrows 68a in FIG. 3B, and then folded as indicated by the arrow 68b in FIG. 3C. The folds reduce each end 63 to a length that fits in a respective sleeve 53 of the clinical garment 22. The folds are preferably made so as to be easily tucked between the clinical garment 22 and the first convective apparatus 60. The ends of the folded configurations may be retained in the inside cuffs 58 in the sleeves of the clinical garment 22. This allows the patient to insert an arm through the sleeve of the clinical garment 22 without catching the corresponding hand on the fold and inadvertently deploying the extended side. Preferably, the ends 63 are folded by a Z-fold, although a gatefold, accordion fold or any equivalent fold may be used. More generally, the ends 63 may be folded, rolled or gathered in any way that achieves the desired length reduction and neat compaction useful for stowing and retaining the ends 63 in the cuffs 58, and unfolding them when the first convective apparatus is to be used for therapeutic warming. The first convective apparatus 60 has a line of weakness or perforation that extends transversely at 69 between each end 63 and a respective laterally-extending side 62.

With further reference to FIGS. 3B and 3C, in some aspects the first convective apparatus 60 may include an attachment mechanism, preferably in the form of double-sided tape 66. Preferably, the double-sided tape 66 is attached on one side of the convective apparatus 60 to a sealed lower portion of the permeable surface 64 of the first convective apparatus 60, along the lower edge 65, centered between the ends 63. Referring to FIG. 3B, the surface 66b of the double-sided tape 66 that is visible is covered with a non-adhesive backing that can be stripped off to expose the adhesive with which both sides of the tape are covered. For convenience, the sealed lower portion of the permeable surface 64 where the attachment mechanism is mounted may be surrounded by a perforation 66p which allows either side of the attachment mechanism to be detached from the sealed lower portion and permit the attachment mechanism to pivot on its longitudinal edge. The perforation 66p also permits the attachment mechanism to be removed after use.

With reference to FIGS. 3B and 3C, although one inlet port 61 is illustrated in the first convective apparatus 60, one or more additional inlet ports may be provided for convenience. Unused inlet ports are sealed or closed by known means to prevent air escaping therethrough. Preferably the inlet port 61 is provided through the surface of the first convective apparatus 60 which is not visible in this figure; it may also be provided through an edge of the first convective apparatus 60. The inlet port 61 may comprise a collar 61a of stiff material with an opening 61b to receive the nozzle of an air hose, or it may comprise a sleeve of material, or any other equivalent structure. When the first convective apparatus 60 is used for therapeutic warming, the ends of the sleeves are removed from the cuffs 58 and unfolded. Then, warmed pressurized air flowing through an inlet port such as the inlet port 61 inflates the first convective apparatus 60, from its central portion to its ends 63.

A second convective apparatus 70 with separately inflatable sections is illustrated in FIG. 3D. A "section" of the second convective apparatus 70 is a portion or division of the second convective apparatus 70 that may be inflated and operated separately from any other section of the second convective apparatus 70. For example, the second convective apparatus 70 has a section 71 and a section 72. The section 71 may be inflated and operated separately from the section 72, and the section 72 may be inflated and operated separately from the section 71.

In the second convective apparatus 70 shown in FIG. 3D, the section 71 has an inlet port 74, an upper edge 75, an elongate central part 76, and upper and lower transverse parts 77 and 78 that connect perpendicularly to the central part 76. The ends of the upper and lower transverse parts 77 and 78 may be rounded, so that, in the plan view of FIG. 3C, the section 71 has a "dog bone" shape. Alternatively, the section 71 may have the shape of a capital I, with upper and lower cross bars. Although one inlet port 74 is illustrated in the section 71, one or more additional inlet ports may be provided for convenience. Unused inlet ports are sealed or closed by known means to prevent air escaping therethrough. Preferably the inlet port 74 is provided through the surface of the second convective apparatus 70 which is not visible in this figure. The inlet port 74 may comprise a collar 74a of stiff material with an opening 74b to receive the nozzle of an air hose, or it may comprise a sleeve of material, or any other equivalent structure. The space in the central part 76 is in fluid communication with the spaces in the transverse parts 77 and 78 so that pressurized air flowing through the inlet port 74 flows throughout the parts 76-78, thereby inflating the first section 71. The surface 79 of the section 71 which is visible in FIG. 3D, including the surfaces of the parts 76-78, is permeable, permitting pressurized air that is flowing into and inflating the section 71 to be expelled toward the interior of the clinical garment 22 (that is, toward a patient wearing the device 20). In some aspects of the first section 71, the permeability of the surfaces of the parts 76-78 may vary in order to reduce or eliminate variances in temperature of air expelled through the permeable surface 79 of the section 71.

As seen in FIG. 3D, the second section 72 has a U-shaped outline with lower edge 82 and side edges 83 and 84. The section 72 generally forms an outline that surrounds the first section 71 on three sides. Although one inlet port 85 is illustrated in the section 72, one or more additional inlet ports may be provided for convenience. Unused inlet ports are sealed or closed by known means to prevent air escaping therethrough. Preferably the inlet port 85 is provided through the surface of the second convective apparatus 70 which is not visible in FIG. 3F, although it may also be provided through an edge of the second convective apparatus 70. The inlet port 85 may comprise a collar 85a of stiff material with an opening 85b to receive the nozzle of an air hose, or it may comprise a sleeve of material, or any other equivalent structure. Pressurized air flowing through the inlet port 85 inflates the section 72. The surface 86 of the section 72 which is visible in FIG. 3F is permeable, permitting pressurized air that is flowing into and inflating the section 72 to be expelled toward the interior of the clinical garment 22 (that is, toward a patient wearing the device 20).

In some aspects of the second convective apparatus 70, shown in FIG. 3D, the lower edge 75 of the first section 71 is adjacent the upper edge 80 of the second convective apparatus in order to position the upper transverse part 77 approximately against and transverse to the upper chest, between the shoulders, of a patient wearing the clinical garment 22. This advantageously locates the upper transverse part 77 for delivery of air for comfort warming the patient.

The dog-bone and U construction of the second convective apparatus 70 is not intended to be limiting; it is just one example of how the apparatus may be provided with separately-inflatable sections for comfort and therapeutic warming, and other possible two-section constructions are shown and described in the related applications that are listed above.

With reference to FIG. 3D, in some aspects of the second convective apparatus 70 the inlet port 74 of the first section 71 may have a smaller opening 74b than the opening 85b through the inlet port 85 of the second section 72. In this case, the openings 61b of the first convective apparatus 60 and 85b of the second section 72 are preferably of equal size. Consequently, the inlet port 74 accepts an air hose nozzle with a smaller diameter than the air hose nozzle diameter accepted by the inlet ports 61 and 85. The smaller nozzle diameter signifies a comfort warming air supply with an air hose having a smaller diameter than the air hose of a therapeutic warming air supply. Further, the smaller air hose may be coupled to a heater/blower unit with a smaller capacity than that of the heater/blower unit of a therapeutic warming air supply, which can be connected to either the first convective apparatus 60 or the second section 72 of the second convective apparatus 70. The provision of an inlet port 74 dimensioned for a smaller-diameter hose enables the first section 71 to operate in response to a lower capacity heater/blower unit designed for comfort warming. The provision of inlet ports 61 and 85 dimensioned for a larger-diameter hose enables the first convective apparatus 60 and the second section 72 of the second convective apparatus 70 to operate in response to a higher capacity heater/blower unit designed for therapeutic warming. The first convective apparatus 60 is therefore constructed for therapeutic warming, and the second convective apparatus 70 has a first section 71 constructed for comfort warming and a second section 72 constructed for therapeutic warming.

FIG. 3D illustrates a preferred relationship between the first and second convective apparatuses 60 and 70 as they are disposed, supported or constructed on the inside surface 43 of the clinical garment 22. The blankets 60 and 70 are disposed such that the upper edge 80 of the second convective apparatus 70 overlaps the lower edge 65 of the first convective apparatus. The upper edge 80 may be retained in place by tacking, taping, or a light adhesive acting between the upper edge 80 and the first convective apparatus 60 and/or the inside surface 43 of the clinical garment.

Preferably, the overlapping upper edge 80 seen in FIG. 3D covers the double-sided tape 66, but it may be folded back from the lower edge 65 to expose the double-sided tape 66 on the first convective apparatus 60. An operation for deploying the double-sided tape for use is shown in FIGS. 3G, 3H, and 3I. In FIG. 3G, the double-sided tape 66 is adhered, on one side, to the first convective apparatus 60 centered along the lower edge 65. Backing is still mounted to the surface 66b that faces the second convective apparatus 70. The upper edge 80 of the second convective apparatus overlaps the lower edge 65 and the double-sided tape 66. When being deployed for use, as seen in FIG. 3H, the two short sections of the perforation 66p (best seen in FIGS. 3B and 3C) are torn. This permits the portion of the first convective apparatus 60 to which the double-sided tape 66 is attached to pivot on its longitudinal edge so that the lower edge 65 with the double-sided tape 66 mounted therealong may be swung outwardly, away from the inside surface of the clinical garment (not shown), over the upper edge 80 of the second convective apparatus 70. As seen in FIG. 3I, the portion of the first convective apparatus 60 to which the double-sided tape 66 is mounted is swung back to lie on the outside of the upper edge 80. In this position, the backing on the surface 66b may be stripped off and the tape 66 may be adhesively attached to the skin of a patient, thereby anchoring the warming device. As explained hereinabove with reference to FIGS. 3B and 3C, the double-sided tape 66 may be removed after use by tearing along the long section of the perforation 66p. Alternatively, the tape 66 may stay be stowed behind the upper edge 80 once the tape has been released from the patient and the upper edge 80 may be adhered to the tape.

A head drape 87, shown furled or folded in FIGS. 3A-3D, preferably constituted of a sheet of clear plastic, may be attached to the inside surface 43 of the clinical garment 22, near the scooped upper edge 54 (shown in FIG. 3A) or may be attached near the upper edge of the first convective apparatus 60 on the surface which faces the inside surface 43 (shown in FIGS. 3B through 3D).

Figure 3E:
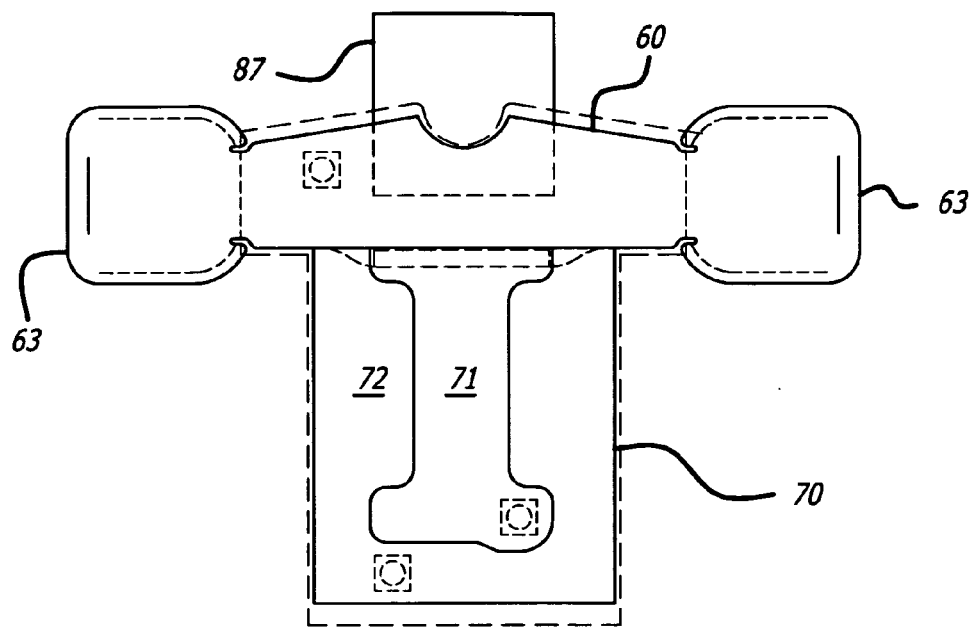
FIG. 3E is a plan view showing the first convective apparatus in the overlapping relationship with the second convective apparatus, with the ends of the first convective apparatus unfolded.
Figures 3G, 3H, 3I:
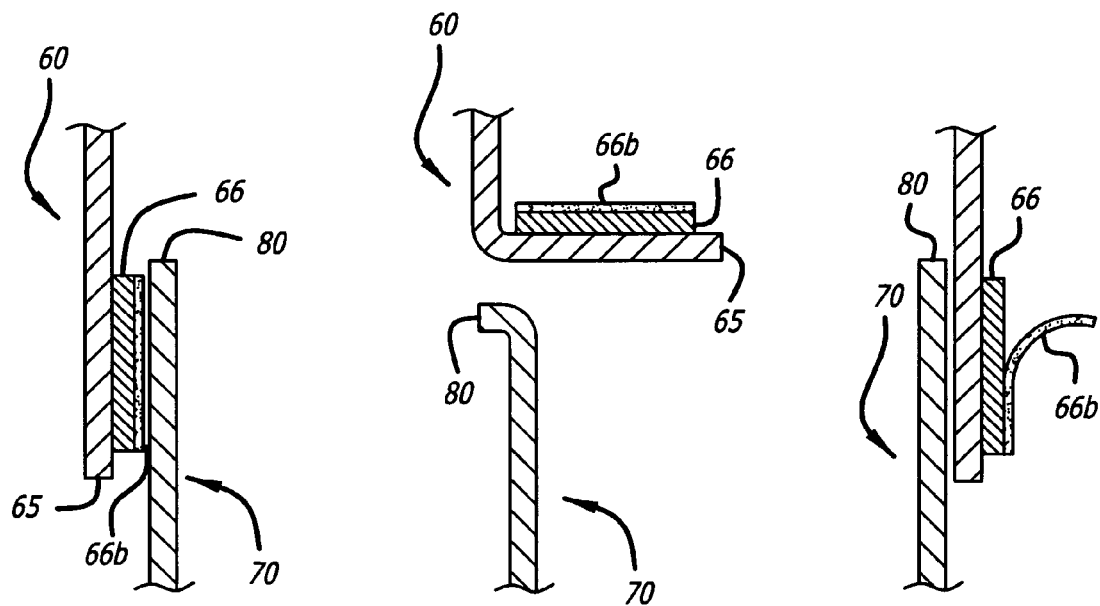
FIGS. 3G through 3I are enlarged, partially schematic views showing an operation of an attachment mechanism.

In FIG. 3E, the plan view shows the convective apparatuses 60 and 70 in the preferred relationship of FIG. 3D, with the ends 63 of the first convective apparatus 60 unfolded, the double-sided tape 66 rotated, and the head drape 87 unfurled.

FIG. 3F shows a multifunction warming device 20 for perioperative use assembled from the elements illustrated in FIGS. 3A-3D. In the multifunction warming device 20, the first and second convective apparatuses 60 and 70 are supported on the inside surface 43 of the clinical garment 22 with the relationship seen in FIG. 3D. In FIG. 3F, the view is toward the permeable surfaces of the convective apparatuses 60 and 70. Together the first and second convective apparatuses 60 and 70 form a Tee-shaped figure, substantially centered on the longitudinal axis 49, and with a thick base (the second convective apparatus 70) and an elongate top (the first convective apparatus 60) which is perpendicular to the base.

As illustrated in FIG. 3F, the first convective apparatus 60 is an elongate convective apparatus disposed, supported, or constructed on the inside surface 43 of the clinical garment 22, in the upper portion 51, transverse to the longitudinal axis 49 and extending from sleeve 53 to sleeve 53. Preferably, the first convective apparatus 60 is an upper body convective apparatus, like an upper body thermal blanket, supported on the inside surface of the clinical garment as described above and having the construction illustrated in FIGS. 3B and 3C, with its ends 63 folded and retained in the inside cuffs 58. An opening in the upper portion 51 of the clinical garment 22 (such as the flap 29 in FIGS. 2 and 3A) provides access by which an air hose can connect to the inlet port 61 of the first convective apparatus 60 in order to operate the convective apparatus 60 for therapeutic warming during thoracic, abdominal, or pelvic surgery. Warmed, pressurized air flows into and inflates the first convective apparatus 60, and exits through the permeable surface 64 toward a patient. The second convective apparatus 70 with separately inflatable sections for therapeutic and comfort warming is disposed, supported, or constructed on the inside surface 43, in the lower portion 55, and is disposed longitudinally to the clinical garment 22, with the longitudinal axis 49 and extending from just above the lower edge 65 of the first convective apparatus 60 toward the lower hem 47. Preferably, the second convective apparatus 70 has the construction illustrated in FIG. 3D with a dog-bone shaped section 71 to provide comfort warming, and a second, separately-inflatable section 72 that frames the dog-bone shaped section 71 to provide therapeutic warming. An opening in the lower portion 55 of the clinical garment 22 (such as the flap 28 in FIGS. 2 and 3A) provides access by which an air hose can connect to the inlet port 74 of the first section 71 of the second convective apparatus 70 to operate the first section for comfort warming. Warmed, pressurized air flows into and inflates the first section 71, and exits through the permeable surface 79 of the first section 71, toward a patient. An opening in the lower portion 55 of the clinical garment 22 (such as the flap 30 in FIG. 2) provides access by which an air hose can connect to an inlet port 85 of the second section 72 of the second convective apparatus 70 to operate the second section for therapeutic warming. Warmed, pressurized air flows into and inflates the second section 72, and exits through the permeable surface 86 of the second section 72, toward a patient.

The first section 71 of the second convective apparatus 70 may be said to be "adapted" for comfort warming by virtue of an average or mean permeability in the surface 79 that is lower than the average or mean permeability in the surface 86 of the second section 72. The lower average permeability of the surface 79 accommodates a lower air pressure entering the first section 71 from a relatively low capacity heater/blower unit, coupled by a smaller-diameter air hose to a smaller inlet port. Similarly, the second section 72 of the second convective apparatus 70 may be said to be "adapted" for therapeutic warming by virtue of an average or mean permeability in the surface 86 that is higher than the average or mean permeability in the surface 79 of the first section 71. The higher average permeability of the surface 86 accommodates a higher air pressure entering the second section 72 from a relatively high capacity heater/blower unit, coupled by a larger-diameter air hose to a larger inlet port.

Each of the first and second convective apparatuses 60 and 70 may be formed by joining two sheets of material with a closed impermeable seam around their peripheries and, in the second convective apparatus, one or more additional closed impermeable seams to define the separate sections. One of the sheets is relatively impermeable and the other sheet is relatively more permeable to permit airflow therethrough. The sheets are further connected by discontinuous seals or stake points within the closed impermeable seams. The two sheets with which a convective apparatus is formed may be separate from the clinical garment 22, in which case the convective apparatuses are permanently or releasably attached, fixed, or adhered to the inside surface 43 of the clinical garment 22, with their permeable surfaces facing inwardly, toward a patient wearing the device 20. An exemplary construction in this regard is illustrated in FIGS. 1A and 1D and FIGS. 3A-3C of PCT publication WO 2003/086500. Alternately, the convective apparatuses may be formed or constructed integrally with a clinical garment 22 made of relatively impermeable material by attaching relatively permeable sheets to portions of the inside surface of the clinical garment 22. An exemplary construction in this regard is illustrated in FIGS. 1D and 1E and FIGS. 3D-3F of PCT publication WO 2003/086500.

According to the present best mode of construction of the multifunction warming device for perioperative use, the first and second convective apparatuses are formed or assembled separately from the clinical garment and then attached to its inside surface by sewing, gluing, heat sealing, or welding, or any combination of these. Each of the first and second convective apparatuses is formed by heat sealing two sheets of material together. The first convective apparatus is formed with a laminate sheet comprising a layer of nonwoven material on which a layer of polypropylene is extruded, and a polypropylene film. Apertures are formed through the laminate sheet and the polypropylene layer and polypropylene film are sealed around their peripheries. The polypropylene film is attached to the inside surface of the clinical garment and the nonwoven material faces the patient. The reason for locating the polypropylene film on the inside surface of the clinical garment is to reduce the bulk and stiffness of the first convective apparatus, thus making the warming device more comfortable to the patient. The sheets used for the second convective apparatus each comprise a layer of spunbond nonwoven material with a polypropylene extrusion coating on one side. This construction is used for both sides of the second convective apparatus. The extrusion coated sides of the sheets are positioned facing the interior inflatable space of the second convective apparatus, away from the patient. The polypropylene extrusion makes the nonwoven material air impermeable. That way the air blown into the second convective apparatus can be dispersed to the patient by selectively perforating the patient side of the second convective apparatus, which forms the permeable surface of the second convective apparatus. The side of the second convective apparatus that faces the inside surface of the clinical garment is nonwoven, and when the patient slides her or his hands into the hand slits 44, they are in comfortable contact with a soft material.

When the multifunction warming device 20 is worn as shown in FIG. 2 for comfort warming, a convective apparatus may be connected to a heater/bower unit via an air hose to receive a stream of warmed pressurized air. The convective apparatus inflates in response to the stream of air and emits air through its permeable surface. The multifunction warming device 20 retains warmed air within the clinical garment 22 for comfort warming preoperatively. Preferably, although not necessarily, the first section 71 of the second convective apparatus 70 is operated for comfort warming preoperatively. When comfort warming is provided by operation of the first section 71, the person being warmed may insert his or her hands through the slits 44 in the front of the clinical garment 22, which open into space between the clinical garment 22 and the surface of the second convective apparatus 70 which faces the inside surface 43 of the clinical garment 22. These slits 44 afford access to a space where the hands can be pre-warmed in preparation for comfort and/or receipt of an IV needle. Alternatively, with reference to FIGS. 3B and 3C, one end 63 of the first convective apparatus 60 may be unfurled or unfolded and extended through the sleeve 53 in which it is disposed to cover the arm and hand of the person wearing the warming device 20. Then, the first convective apparatus 60 may be inflated by way of the inflation port under the flap 29 with a stream of warm air to pre-warm the arm and hand for receipt of an IV needle.

Figure 4A:
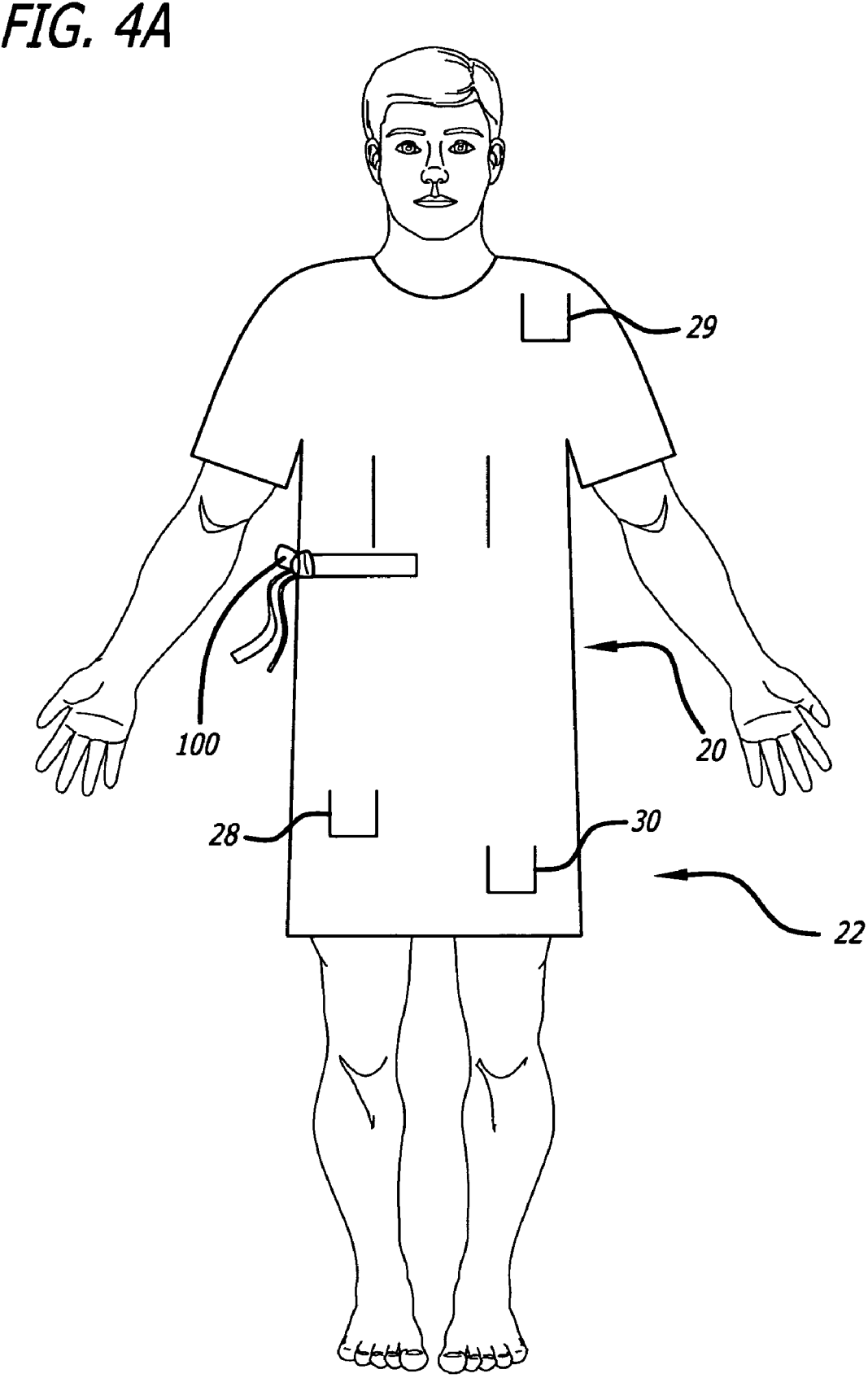
FIGS. 4A-4D illustrate preparation and deployment of a multifunction warming device to therapeutically warm respective body portions of a patient.
Figure 4B:
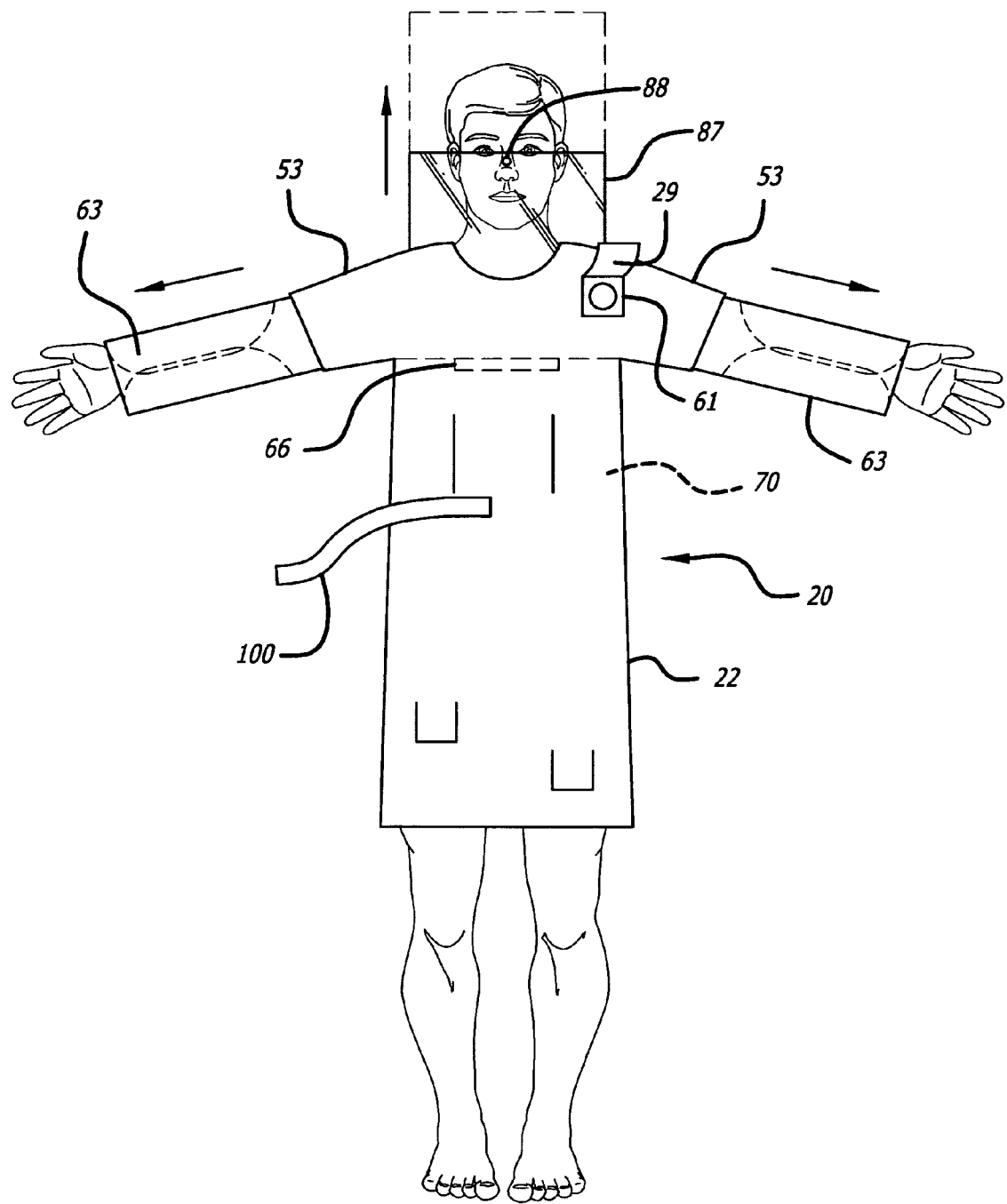
Figure 4C:
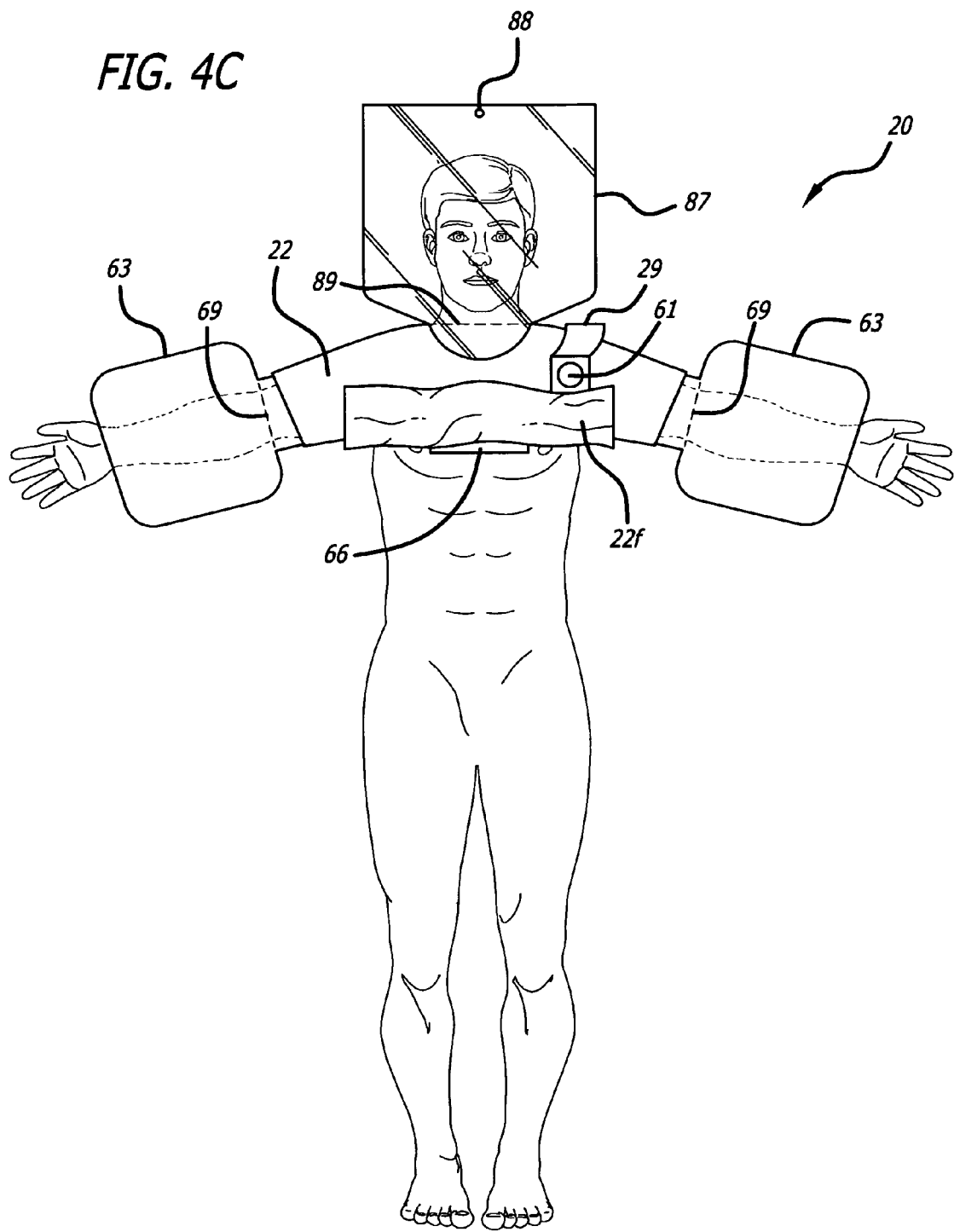

FIGS. 4A-4C illustrate how the multifunction warming device 20 is adapted for therapeutic warming by using the first convective apparatus 60 in the same manner as an upper body thermal blanket. The view in these figures is toward the front of the clinical garment 22, from a position above the patient, who is lying prone on an operating table (not shown), preferably one with cruciate support for the patient's arms. In FIG. 4A, a patient is shown wearing a warming device 20 as preparation commences Ties 100 hold the clinical gown 22 closed. In FIG. 4B, the ties 100 are untied, and the head drape 87 is unfurled, as are the ends 63 of the first convective apparatus 60. A grasping target 88 (also seen in FIGS. 3B-3E), or a tab, not shown, may be provided on a free upper edge of the head drape 87 so that the drape may be grasped for deployment. The ends 63 are freed from the cuffs 58, unfurled through the ends of the sleeves 53 and unfolded to be positioned over the hands and wrists of the patient.

In FIG. 4C, the flap 29 has been folded back to expose the inlet port 61 of the first convective apparatus 60 and a heater/blower unit (not shown) may now be connected to the inlet port 61 via an air hose and nozzle (not shown). As explained above in connection with FIGS. 3G, 3H, and 3I the double-sided tape 66 is deployed for use. That is to say, the upper edge of the second convective apparatus 70 is pulled away from the double-sided tape 66 and the backing 66b is pulled off the tape's outer surface. As seen in FIG. 4C, the ends 63 of the first convective apparatus 60 and head drape 87 are fully unfurled, the tape 66 is adhesively attached to the patient's body, and the lower portion of the clinical garment 22 is furled or folded at 22f, together with the second convective apparatus 70, over the first convective apparatus 60, thereby removing the lower portion of the multifunction warming device 20 from the surgical site. FIG. 4C shows the first convective apparatus 60, in the form of an upper body convective device, freed for deployment over and secured to the patient, and operated thereat to provide therapeutic warming during thoracic, abdominal, or pelvic surgery. In operation, the first convective apparatus 60 inflates in response to a stream of air from a heater/blower unit and emits air through its permeable surface toward the patient. The head drape 87 and unfurled ends 63 trap warm air around the patient's head and hands, which contributes to maintaining the core temperature at or near normothermia.

Figure 5A:
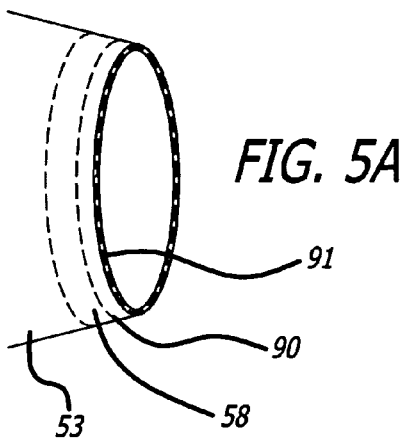
FIGS. 5A-5E are views of the front of the left sleeve of the clinical garment, looking toward the front surface of the clinical garment, showing lines of weakness that may be operated to provide access to ends of the first convective apparatus.
Figure 5B:
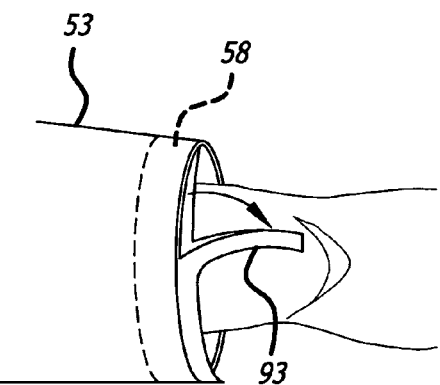
Figure 5C:
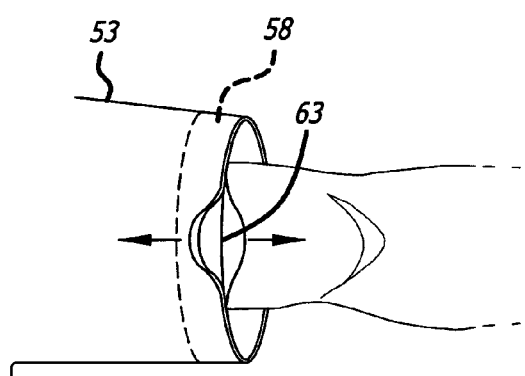
Figure 5D:
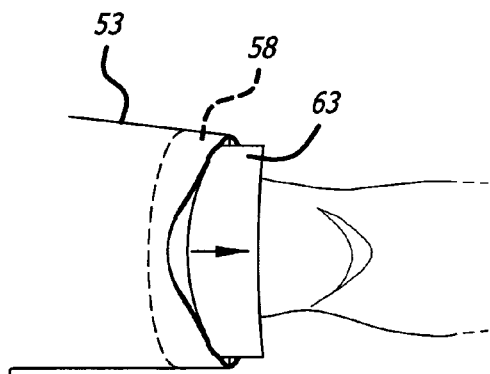
Figure 5E:
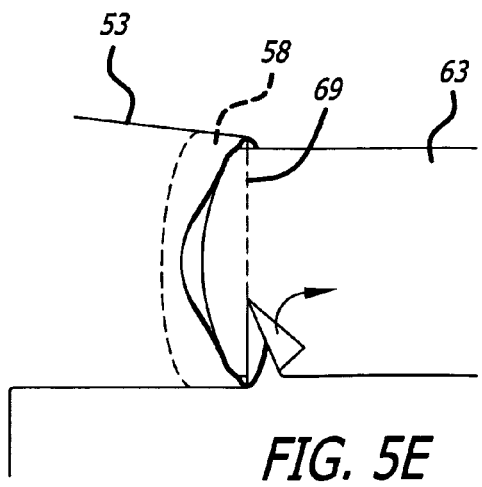

With reference to FIG. 4C, after surgery, when the heater/blower unit is disconnected from the first convective apparatus 60, the ends 63 may be removed along the perforations 69 seen in FIGS. 3B, 4C, and 5E, or the first convective apparatus 60 may left intact to continue being used for warming in the postoperative period. The upper portion of the head drape 87 may be detached along the line of perforations 89 seen in FIG.

4C, or the head drape may be left intact to continue being used for warming in the postoperative period. With reference to FIG. 4C, the furled portion 22f of the clinical garment 22 may be unfurled or unfolded, together with the second convective apparatus 70, from the center of the first convective apparatus 60 toward the patient's feet thereby reconfiguring the clinical gown 22 to be worn again by the patient. Alternatively, if the patient is to be warmed postoperatively while recovering from anesthesia, the unfurled clinical gown 22 can serve as a blanket or drape over the patient to trap warm air about the patient.

Figure 4D:
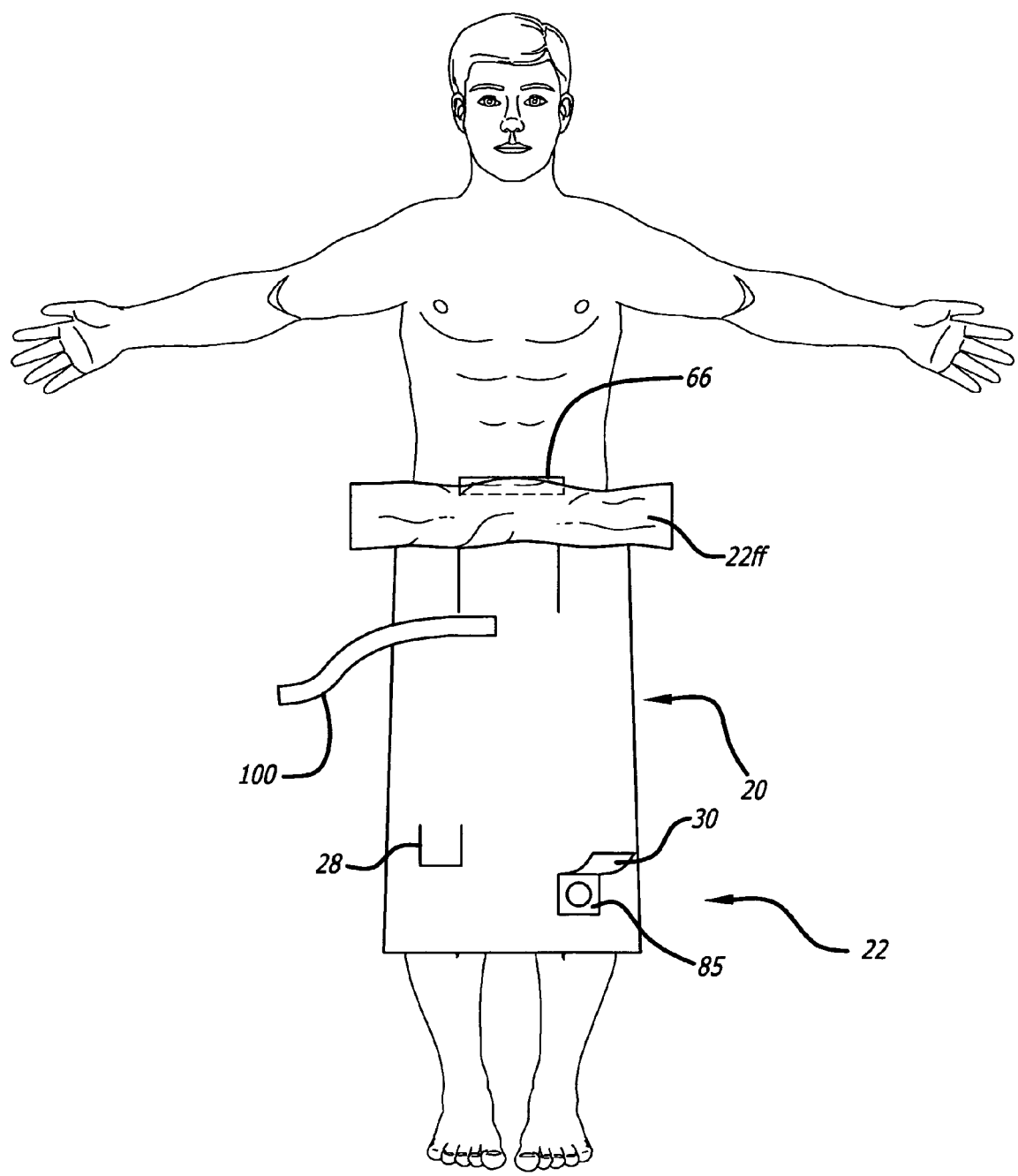

FIG. 4D illustrates how the multifunction warming device 20 is adapted for therapeutic warming using the second convective apparatus 70 to warm the patient in the same manner as a lower body thermal blanket during surgery. The view is toward the front of the clinical garment 22, from a position above the patient, who is lying on an operating table (not shown), preferably one with cruciate support for the patient's arms. The multifunction warming device 20 may be configured as shown in FIG. 4D for therapeutic warming using the second section 72 of the second convective apparatus 70 by separating the sleeve seams 56 and pulling the sleeves away from the patient's arms. The upper portion 51 of the clinical garment 22 is then pulled down from the patient's upper body and furled or folded at 22ff, with the first convective apparatus 60, over the lower portion 55. The ties 100 are untied to loosen the clinical garment 22, and the clinical garment 22 may be slid toward the patient's feet if required to clear the surgical site The tape of the attachment mechanism 66 is deployed for use as explained above in connection with FIGS. 3G, 3H, and 3I, the backing 66b is removed and the tape is adhesively attached to the patient's body. The flap 30 is folded back to expose the inlet port 85 of the second section 72 and a heater/blower unit (not shown) is connected to the inlet port 85 via an air hose and nozzle (not shown). The second convective apparatus 70 is thus deployed and used in the same manner as a lower body thermal blanket during surgery on the patient's upper body, using the second section 72. The sides of the clinical gown 22 may be allowed to hang and act as a drape, trapping warmed air around the patient. After surgery, the clinical garment 22 may be slid toward the patient's upper chest where the upper portion 51 may be unfurled or unfolded, together with the first convective apparatus 60, from the lower portion 55 toward the patient's shoulders. The sleeves 53 may be pulled upwardly over the patient's shoulders, and the seams 56 may be joined around the shoulders and upper arms to reconfigure the clinical gown 22 to be worn by the patient. Alternatively, if the patient is to be warmed postoperatively while recovering from anesthesia, the unfurled clinical gown 22 can serve as a blanket or drape over the patient to trap warm air about the patient.

The best current mode for unfurling the folded ends 63 of the first convective apparatus through the ends of the sleeves 53 may be understood with reference to FIGS. 5A-5E, in which the view is toward the front surface of the left sleeve of the clinical garment 22. Thus, although it uses the left sleeve for illustration, the following explanation also applies to a corresponding construction of the right sleeve. FIG. 5A shows lines of weakness (preferably, perforations) formed in the sleeve 53 to enable access to an end 63 folded and tucked into a cuff 58. Two opposing lines of perforations 90 may be formed near the end of the sleeve 53, one in the front half of the sleeve, and an opposing one in the half of the cuff 58 that faces the front half of the sleeve. Alternately, a single line of perforations 91 may be formed at or near the end of the sleeve, where the sleeve transitions into the cuff 58. As best seen in FIG. 5B, the first pattern of perforations 90 enables a user to tear away the end 93 of the front half of the sleeve 53. The second pattern of perforations 91 permits a user to separate the two sides of the end of a sleeve, at or near the end of the sleeve 53 in the manner illustrated in FIG. 5C. As seen in FIG. 5D, once the end of a sleeve 53 is opened, the folded portion of the end 63 of the first convective apparatus 60 can be pulled through the now-opened end of the cuff 58, through the end of the sleeve 53.

The best current mode for forming the cuffs 58 inside the sleeves 53 with respect to lines of perforation 90 or 91 may be understood with reference to FIGS. 3A, 3D, 3F, and 5A-5C. In this regard, the preferred pattern of perforations is formed in the front halves of the sleeves 53 of the clinical garment 22. The first and second convective apparatuses 60 and 70 are formed separately from the clinical garment 22 as described above. The first convective device 60 is brought against the inside surface 43 in the fully folded configuration shown in FIG. 3D, running between the sleeves 53, with its impermeable surface facing the inside surface 43 and the folded configurations of the ends 63 located therebetween. The first convective apparatus 60 is attached to the inside surface 43 by lines of adhesive bonding between its upper and lower edges and the portion of the inside surface in the front halves of the sleeves 53. Toward the ends of the sleeves, the lines of adhesive bonding stop short of the folded portions of the ends 63 and the perforations 90; in the direction of the longitudinal axis 49, the lines of bonding stop where the sleeves 53 join the main body of the clinical garment 22. A line of adhesive stake points between the impermeable surface of the first convective apparatus 60 and the inside surface is provided just above the attachment mechanism 66. The end of each sleeve 53 is then folded inwardly of the sleeve 52, toward and along the inside surface 43, far enough to position the two lines of perforations 90 opposite each other, one line inside and the other line outside of the sleeve, or to position the single line of perforations 91 at or near the transition to the inside cuff 58. Once folded, the end of each sleeve is attached inside the sleeve by a single elongate strip of adhesive bonding extending transversely across the sleeve. With reference to FIGS. 3A and 3D, the strip of bonding for each cuff 58 may be as wide as the cuff. As may be further appreciated with reference to these figures, the strip of adhesive bonding along a cuff 58 runs between the cuff and a trace extending from a portion of the inside surface 43 in the sleeve 53 above the upper edge 62 of the first convective apparatus 60, across a narrow strip of the permeable surface 64 of the first convective apparatus 60 in the front half of the sleeve, and across a narrow strip of the inside surface in the back half of the sleeve. When the perforation pattern near or at the end of a sleeve 53 is opened, the user reaches into the space defined between the front of the sleeve and the impermeable surface of the first convective apparatus 60, grasps the folded end portion of the first convective device stowed therein, and unfolds the folded end portion out through the opening. This construction interferes minimally with the operation of the first convective apparatus 60 since the strip of adhesive bonding occludes only small strips of the permeable surface of the apparatus. At the same time, this construction serves to secure the ends 63 of the first convective apparatus 60 against movement with respect to the sleeves 53 of the clinical garment 22.

A multifunction warming device is constituted of a clinical garment and two convective apparatuses supported on an inside surface of the garment. A first convective apparatus is disposed transversely in an upper portion of the clinical garment, running between the sleeves of the clinical garment. Advantageously, the positioning of the first convective apparatus in the clinical garment locates it against the chest of a patient wearing the garment and permits it to be deployed and used on the patient's upper body during and after surgery without removal of the clinical garment from the patient or removal of the convective apparatus from the gown. The second convective apparatus is disposed longitudinally in a lower portion of the clinical garment and has separately inflatable sections, each for enabling a particular mode of warming. With the convective apparatuses supported on the inside surface of the garment, the device can be worn by the patient as a clinical gown, and comfort warming can be provided by operation of one section of the second convective apparatus. In preparation for surgery, one of the convective apparatuses is deployed for therapeutic warming while the clinical garment, with the unused convective apparatus, is furled or folded over or around the convective apparatus deployed for therapeutic warming during surgery. The clinical garment may be unfurled or unfolded to be again worn by or draped over the patient postoperatively.

Although the invention has been described with reference to the presently preferred embodiment, it should be understood that various modifications can be made without departing from the spirit of the invention. Accordingly, the invention is limited only by the following claims.

The invention claimed is:

1. A warming device for perioperative use, comprising:
   a clinical garment having an inside surface, an upper portion with opposing sleeves, and a lower portion;
   a first convective apparatus for providing warming by convection, the first convective apparatus supported on the inside surface, in the upper portion; and
   a second convective apparatus supported on the inside surface, in the lower portion;
   the second convective apparatus including at least first and second separately inflatable sections, the first section for providing comfort warming by convection and the second section for providing therapeutic warming by convection.

2. The warming device of claim 1, wherein the first convective apparatus is an elongate convective apparatus, the warming device further including an inlet port in the first convective apparatus.

3. The warming device of claim 2, wherein the first convective apparatus is disposed transversely across the upper portion, extending from sleeve to sleeve.

4. The warming device of claim 2, wherein the first convective apparatus includes two laterally-extending sides, each side being disposed in a folded configuration in a respective sleeve.

5. The warming device of claim 4, each sleeve including an inside cuff retaining a side in the folded configuration, and one or more lines of perforation near the cuff for being opened to provide access through the end of the sleeve to the side in the folded configuration.

6. The warming device of claim 4, further including means in each sleeve for releasably retaining a side in the folded configuration in the sleeve.

7. The warming device of claim 4, wherein the first convective apparatus includes perforation lines extending transversely across each side.

8. The warming device of claim 7, each side including an end of the first convective apparatus, and each side being extendable from the folded configuration to an unfolded configuration in which the end extends outwardly from the clinical garment.

9. The warming device of claim 8, wherein the perforation lines on a side enable the separation of an end from the first convective apparatus.

10. The warming device of claim 2, wherein the first convective apparatus includes opposing ends and ties formed in the ends.

11. The warming device of claim 10, wherein the ties include arcuate shapes.

12. The warming device of claim 2, wherein the first convective apparatus includes opposing ends and end slits near the ends for receiving the hands of a person.

13. The warming device of claim 1, wherein the first section includes a bone-shaped part and an inlet port in the bone-shaped part, and the second section includes a U-shaped part that surrounds the bone-shaped part on three sides and an inlet port in the U-shaped part larger than the inlet port in the bone-shaped part.

14. The warming device of claim 1, further including an upper edge on the first convective apparatus and a head drape near the upper edge.

15. The warming device of claim 1, wherein the first convective apparatus includes at least one inlet port, the first section includes at least one inlet port, and the second section includes at least one inlet port, the inlet ports of the first convective apparatus and the second section having dimensions to receive a warming hose nozzle of a first diameter and the inlet ports of the first section having a dimension to receive a warming hose nozzle of a second diameter smaller than the first diameter.

16. The warming device of claim 1, wherein the clinical garment includes opposing lateral hems defining an opening, and a tie formed in the clinical garment near an end of each hem.

17. A multifunction warming device, comprising:
   a clinical garment having an upper portion with opposing sleeves, and a lower portion;
   an upper body convective apparatus attached inside of the upper portion;
   a lower convective apparatus attached inside of the lower portion; and
   the lower convective apparatus including at least two separately inflatable sections, a first section for providing comfort warming by convection and a second section for providing therapeutic warming by convection.

18. The multifunction warming device of claim 17, wherein the upper body convective apparatus includes an upper edge, the multifunction warming device further including a head drape attached along the upper edge.

19. The multifunction warming device of claim 17, wherein the upper body convective apparatus includes two laterally-extending sides, each side disposed in a folded configuration in a respective sleeve.

20. The multifunction warming device of claim 19, each sleeve including an inside cuff, each cuff retaining a side in the folded configuration, and one or more lines of weakness near the cuff for being opened to provide access through the end of the sleeve to the side in the folded configuration.

21. The multifunction warming device of claim 19, the upper body convective apparatus includes a line of weakness extending transversely across each side.

22. The multifunction warming device of claim 17, wherein the upper body convective apparatus includes two ends, each end including a line of weakness transverse to the upper body convective apparatus for separating the end from the upper body convective apparatus.

23. The multifunction warming device of claim 17, wherein the lower convective apparatus is disposed longitudinally along the lower portion, the first section includes a bone-shaped part and an inlet port in the bone-shaped part, the second section includes a U-shaped part that surrounds the bone-shaped part on three sides and at least one inlet port in the U-shaped part.

24. The multifunction warming device of claim 17, wherein the upper body convective apparatus includes a first inlet port, the first section includes a second inlet port, and the second section includes a third inlet port, the first and third inlet ports having dimensions to receive a warming hose nozzle of a first diameter and the second inlet port having a dimension to receive a warming hose nozzle of a second diameter smaller than the first diameter.

25. The warming device of claim 24, wherein the first section includes a bone-shaped part and an inlet port in the bone-shaped part, and the second section includes a U-shaped part that surrounds the bone-shaped part on three sides, and at least one inlet port in the U-shaped part.

* * * * *

UNITED STATES PATENT AND TRADEMARK OFFICE
CERTIFICATE OF CORRECTION

| | | |
|---|---|---|
| PATENT NO. | : 7,819,911 B2 | Page 1 of 1 |
| APPLICATION NO. | : 11/583432 | |
| DATED | : October 26, 2010 | |
| INVENTOR(S) | : Thomas P Anderson | |

It is certified that error appears in the above-identified patent and that said Letters Patent is hereby corrected as shown below:

Column 2
Line 40, delete "and" and insert -- and, --, therefor.

Column 20
Line 3, in Claim 25, after "The" insert -- multifunction --.

Signed and Sealed this
Fourth Day of September, 2012

David J. Kappos
*Director of the United States Patent and Trademark Office*